(12) United States Patent
Clemmens et al.

(10) Patent No.: US 7,763,453 B2
(45) Date of Patent: Jul. 27, 2010

(54) MICROFLUIDIC MIXING AND ANALYTIC APPARATUS

(75) Inventors: John Clemmens, Redmond, WA (US); C. Frederick Battrell, Redmond, WA (US); John Gerdes, Columbine Valley, CO (US); Denise Maxine Hoekstra, Monroe, WA (US)

(73) Assignee: Micronics, Inc., Redmond, WA (US)

( * ) Notice: Subject to any disclaimer, the term of this patent is extended or adjusted under 35 U.S.C. 154(b) by 669 days.

(21) Appl. No.: 11/562,611

(22) Filed: Nov. 22, 2006

(65) Prior Publication Data

US 2007/0183935 A1    Aug. 9, 2007

Related U.S. Application Data

(60) Provisional application No. 60/740,697, filed on Nov. 30, 2005.

(51) Int. Cl.
*C12M 1/36* (2006.01)
(52) U.S. Cl. .............. 435/286.7; 435/288.2; 435/288.5; 422/50; 422/104
(58) Field of Classification Search ........................ None
See application file for complete search history.

(56) References Cited

U.S. PATENT DOCUMENTS

| | | | |
|---|---|---|---|
| 3,933,997 A | 1/1976 | Hersh et al. | |
| 3,970,518 A | 7/1976 | Giaever | |
| 4,018,886 A | 4/1977 | Giaever | |
| 4,230,685 A | 10/1980 | Senyei et al. | |
| 4,267,234 A | 5/1981 | Rembaum | |
| 4,452,773 A | 6/1984 | Molday | |
| 4,554,088 A | 11/1985 | Whitehead et al. | |
| 4,654,267 A | 3/1987 | Ugelstad et al. | |
| 4,659,678 A | 4/1987 | Forrest et al. | |
| 5,716,852 A | 2/1998 | Yager et al. | |
| 6,432,212 B1 | 8/2002 | Hirose et al. | |
| 6,581,899 B2 | 6/2003 | Williams | |
| 2002/0029814 A1* | 3/2002 | Unger et al. ................ 137/824 |
| 2002/0148992 A1 | 10/2002 | Hayenga et al. | |
| 2002/0187560 A1* | 12/2002 | Pezzuto et al. .............. 436/180 |

(Continued)

FOREIGN PATENT DOCUMENTS

WO      WO 02/40874 A1      5/2002

(Continued)

OTHER PUBLICATIONS

Carter et al., "Short Exposure Time Sensitivity of White Cells to Shear Stress", ASAIO Journal 49: 687-691, 2003.

(Continued)

*Primary Examiner*—Nelson C. Yang
(74) *Attorney, Agent, or Firm*—Seed IP Law Group PLLC

(57) ABSTRACT

Disclosed herein is a device comprising a pair of bellows pumps configured for efficient mixing at a microfluidic scale. By moving a fluid sample and particles in suspension through an aperture between the paired bellows pump mixing chambers, molecular collisions leading to binding between the particles and ligands in the sample are enhanced. Such devices provide an alternative for mixing that does not use a vent and can be used with a variety of particles in suspension such as magnetic beads to capture or purify useful cells and molecules.

15 Claims, 11 Drawing Sheets

U.S. PATENT DOCUMENTS

| | | |
|---|---|---|
| 2003/0119057 A1* | 6/2003 | Gascoyne et al. ............ 435/7.1 |
| 2003/0175980 A1 | 9/2003 | Hayenga et al. |
| 2004/0037739 A1 | 2/2004 | McNeely et al. |
| 2006/0246575 A1 | 11/2006 | Lancaster et al. |

FOREIGN PATENT DOCUMENTS

| | | |
|---|---|---|
| WO | WO 03/015923 A1 | 2/2003 |

OTHER PUBLICATIONS

Dewitz et al., "Mechanical trauma in leukocytes", J. Lab. Clin. Med. 90(4): 728-736, Oct. 1977.

Fuentes et al., "Detecting minimal traces of DNA using DNA covalently attached to superparamagnetic nanoparticles and direct PCR-ELISA", Biosensors and Bioelectronics 21: 1574-1580, 2006.

Hashimoto, "Erythrocyte Destruction under Periodically Fluctuating Shear Rate: Comparative Study with Constant Shear Rate", Artificial Organs 13(5): 458-463, 1989.

Kameneva et al., "Effects of Turbulent Stresses upon Mechanical Hemolysis: Experimental and Computational Analysis", ASAIO Journal 50: 418-423, 2004.

Lu et al., "Microfluidic Shear Devices for Quantitative Analysis of Cell Adhesion", Analytical Chemistry 76(18): 5257-5264, Sep. 15, 2004.

Matas et al., "Transition to turbulence in particulate pipe flow", Phys. Rev. Lett. 90:14501-14505, 2003.

Platt, "Exercise-Induced Hemolysis in Sickle Cell Anemia: Shear Sensitivity and Erythrocyte Dehydration", Blood 59(5): 1055-1060, May 1982.

Schmid-Schoenbein et al., "Microscopy and viscometry of blood flowing under uniform shear rate (rheoscopy)", Journal of Applied Physiology 26(5): 674-678, May 1969.

Sirigireddy et al., "Multiplex Detection of Ehrlichia and Anaplasma Species Pathogens in Peripheral Blood by Real-Time Reverse Transcriptase-Polymerase Chain Reaction", Journal of Molecular Diagnostics 7(2): 308-316, May 2005.

Staben et al., "Particle transport in Poiseuille flow in narrow channels", International Journal of Multiphase Flow 31: 529-547, 2005.

Wolf et al., "Rapid hybridization kinetics of DNA attached to submicron latex particles", Nucleic Acids Research 15(7): 2911-2926, 1987.

* cited by examiner

MICROFLUIDIC MIXING AND ANALYTIC APPARATUS

CROSS-REFERENCE TO RELATED APPLICATION

This application claims the benefit under 35 U.S.C. §119 (e) of U.S. Provisional Patent Application No. 60/740,697 filed Nov. 30, 2005, which provisional application is incorporated herein by reference in its entirety.

STATEMENT OF GOVERNMENT INTEREST

This invention was made with government support under Contract Nos. R44 CA105539 and U01 AI061187, both awarded by the National Institutes of Health. The government has certain rights in this invention.

BACKGROUND OF THE INVENTION

1. Field of the Invention

The present invention relates generally to microfluidic devices for mixing suspensions of affinity capture beads in fluidized biological samples, and for apparatuses and methods for ligand capture, depletion, preconcentration, washing, and labeling, followed by analysis, by means of affinity capture beads.

2. Description of the Related Arts

Biological analytes of relevance to clinical, biological, or environmental testing frequently are found at low concentrations in complex fluid mixtures. It is important to capture, concentrate, and enrich the specific analyte away from background inhibitory or interfering matrix components that can limit the sensitivity and/or specificity of analyte detection assays. Specific analytes include but are not limited to nucleic acids, proteins, including for example antigens or antibodies, prokaryotic or eukaryotic cells, and viruses, and small molecules such as drugs and metabolites. Conventional sample preparation methods include centrifugation, solid phase capture, selective precipitation, filtration, and extraction. These methods are not generally amenable to efficient automation and integration with subsequent assay steps, especially in a manner compatible with the development of point of care testing.

Another proven method for preparation of samples takes advantage of magnet fields to capture magnetic particles that have been derivatized to bind a ligand that is linked to the analyte of interest (i.e., capture), or a ligand that is linked to an inhibitor or interference (i.e., depletion). Both methods have been used to prepare the analyte of interest for detection.

Magnetic particles have found a number of uses in biomedical research and diagnostics. A seminal procedure for magnetic capture of cells, bacteria, and viruses is disclosed in U.S. Pat. Nos. 3,970,518 and 4,018,886. The method according to this invention for sorting out and separating a select cell population from a mixed cell population comprises the steps of applying to the surface of small magnetic particles a coating of an antibody to the select cell, bacteria or virus population: moving these antibody-coated magnetic particles through a liquid containing the mixed population whereby the members of the cell, bacteria or virus population become affixed to the antibody coatings on the particles, and separating the coated magnetic beads with such members attached thereto from the rest of the mixed population. These methods also included a "cleaving" step for releasing the bound members. Mixing is provided by an impeller mounted in a modified funnel. Typical incubation times were said to be less than an hour to as much as a day, the lower the concentration, the longer the incubation required. Magnetic particles were said to include ferrites, perovskites, chromites, or magnetoplumbites, and more generally, ferromagnetic, ferrimagnetic or superparamagnetic particles, although it is obvious that permanently magnetic particles will readily clump whereas superparamagnetic particles remain monodisperse until a magnetic field is applied. Hersh, in U.S. Pat. No. 3,933,997 described the use of magnets to capture digoxin from solution.

Other patents describing analytical applications for magnetic particles include U.S. Pat. Nos. 4,018,886; 4,230,685; 4,267,234; 4,452,773; 4,554,088; and 4,659,678. Recent literature citations include: Shaikh K A et al. 2005. A modular microfluidic architecture for integrated biochemical analysis. PNAS 102; 9745-9750; Fuentes M et al. 2006. Detecting minimal traces of DNA using DNA covalently attached to superparamagnetic nanoparticles and direct PCR-ELISA. Biosensors Bioelectronics 21:1574-1580, and Sirigireddy K R and Ganta R R. 2005. Multiplex detection of Ehrlichia and Anaplasma species pathogens in peripheral blood by real-time reverse-transcriptase-polymerase chain reaction. J Mol Diagnostics 7:308-316.

Magnetic beads can be classified on the basis of size as large (1.5 to about 50 microns), small (0.7-1.5 microns), or colloidal (<200 nm), which are also referred to as nanoparticles. Typical of large magnetic beads (>1.5 microns to about 50 microns) are those described by Ugelstad in U.S. Pat. No. 4,654,267 and manufactured by Dynal® (Oslo, Norway). The Ugelstad process involves the synthesis of polymer beads which are caused to swell and magnetite crystals are embedded in the swelled beads.

Large magnetic beads have been found to be advantageous especially when added to viscous or particulate specimens such as feces or blood since they are readily separated with simple laboratory magnets because of the mass of magnetic material per particle. However, limitations of their use occur since these large particles are not colloidal, and do not diffuse. Consequently, the specimen volume and selectivity of capture requires incubation times and adequate mixing to enable the molecular collision of the analyte with the capture particle. Mixing is also critical to subsequent wash steps. Tube methods exhibit inconsistent and long (15-90 minute) mixing and are not readily automated and integrated within an assay method.

Magnetic beads for affinity capture and bead capture devices are readily available, for example from: Dynal Biotech ASA, Oslo, Norway; BD Biosciences, San Jose Calif.; and New England Biolabs, Beverly, Mass., among others. The Dynal ClinExVivo MPC® typifies the capture devices, which rely on rocking or rotation for mixing.

Monodisperse, non-colloidal, latex beads and ion exchange beads have also been used in preconcentration steps for detection of biological analytes. Sedimentation fractionation of DNA with derivatized latex particles was demonstrated as early as 1987 (Wolf S F et al. 1987. Rapid hybridization kinetics of DNA attached to submicron latex particles. Nucl Acids Res 15:2911-2926). These particles demonstrated improved capture kinetics of specific targets as compared to planar solid supports and could be concentrated by centrifugation or filtration. Non-specific DNA capture may be achieved with polyethyleneimine or polyvinylpyrrolidone beads, for example.

Microfluidic devices have become popular in recent years for performing analytical testing. Using tools developed by the semiconductor industry to miniaturize electronics, it has become possible to fabricate intricate fluid systems which can be inexpensively mass produced. Systems have been developed to perform a variety of analytical techniques for the acquisition and processing of information.

The ability to perform analyses microfluidically provides substantial advantages of throughput, reagent consumption, and automatability. Another advantage of microfluidic systems is the ability to integrate a plurality of different operations in a single "lap-on-a-chip" device for performing processing of reactants for analysis and/or synthesis. Microfluidic devices may be constructed in a multi-layer laminated structure wherein each layer has channels and structures fabricated from a laminate material to form microscale voids or channels where fluids flow. A microscale or microfluidic channel is conventionally defined as a fluid passage which has at least one internal cross-sectional dimension that is less than 500 μm and typically between about 0.1 μm and about 500 μm.

U.S. Pat. No. 5,716,852, hereby incorporated by reference in its entirety, is an example of a microfluidic device. The '852 patent teaches a microfluidic system for detecting the presence of analyte particles in a sample stream using a laminar flow channel having at least two input channels which provide an indicator stream and a sample stream, where the laminar flow channel has a depth sufficiently small to allow laminar flow of the streams and length sufficient to allow diffusion of particles of the analyte into the indicator stream to form a detection area, and having an outlet out of the channel to form a single mixed stream. This device, which is known as a T-Sensor, allows the movement of different fluidic layers next to each other within a channel without mixing other than by diffusion. A sample stream, such as whole blood, a receptor stream, such as an indicator solution, and a reference stream, which may be a known analyte standard, are introduced into a common microfluidic channel within the T-Sensor, and the streams flow next to each other until they exit the channel. Smaller particles, such as ions or small proteins, diffuse rapidly across the fluid boundaries, whereas larger molecules diffuse more slowly. Large particles, such as blood cells, show no significant diffusion within the time the two flow streams are in contact.

Many different types of valves for use in controlling fluids in microscale devices have been developed. For example, U.S. Pat. No. 6,432,212 describes one-way valves for use in laminated microfluidic structures, U.S. Pat. No. 6,581,899 describes ball bearing valves for use in laminated microfluidic structures, and U.S. patent application Ser. No. 10/114,890, which application is assigned to the assignee of the present invention, describes a pneumatic valve interface, also known as a zero dead volume valve, for use in laminated microfluidic structures. The foregoing patents and patent applications are hereby incorporated by reference in their entirety.

There is general agreement that, in the laminar flow regime characteristic of microfluidic channels, mixing is limited to diffusion. Because of the dimensions involved, wherein diffusional free path lengths are roughly equal the device dimensions, diffusional mixing can be very effective for solutes. This condition enables ribbon flow, T-sensor, and other useful microfluidic phenomena. However, for larger analytes such as cells, bacteria, viral particles, and for macromolecular complexes and linear polymers, diffusional mixing is slow and processes for capture or depletion of these species require prolonged incubation. Diffusional limits on mixing thus present a problem in microfluidic devices where bulk mixing or comminution of a sample and reagents or beads is required. This problem has not been fully solved and methods, devices and apparatuses for improving the mixing arts are being actively sought.

SUMMARY OF THE DISCLOSURE

In brief, the present invention relates to microfluidic devices, apparatuses, and methods involving manipulating and mixing fluidized biological samples with beads in suspension. The disclosed microfluidic devices and apparatuses utilize a plurality of microfluidic channels, inlets, valves, filters, pumps, liquid barriers and other elements arranged in various configurations to manipulate the flow of a fluid sample to prepare samples for subsequent analysis. Capture and depletion techniques are demonstrated. Analysis of the sample may then be performed by any detection means known in the art. For example, as disclosed herein, microfluidic devices of the present invention may be used to comminute and mix feces or other complex samples with magnetic capture particles for the enrichment of specific target bacteria or viruses, or may be used to capture rare tumor cells or molecular markers from blood and other bodily fluids with various affinity capture beads.

A preferred embodiment disclosed herein is a pair of bellows pumps configured for efficient mixing of particles in suspension at a microfluidic scale. An aperture fluidically connects the bellows pump chambers. As described below, reciprocating pump flow of the suspension through the aperture promotes turbulent mixing and molecular collision of affinity capture particles with ligands as an aid in capture of useful cells and molecules. Such mixing elements provide an alternative for mixing that does not use a vent and enables efficient mixing of small or larger volumes containing particles such as magnetic beads from 0.2 to 100 um in size, more preferably from 1.5 to 50 um, and other beads such as latex and ion exchange polymers. These paired bellows pump mixing elements are combined with other microfluidic structures in microfluidic devices and apparatuses.

In one embodiment, a microfluidic cartridge is provided comprising: (a) a first bellows pump with a pump cavity bisected in coronal plane by a first elastomeric diaphragm, said first diaphragm dividing said pump cavity of said first bellows pump into a first half-chamber and a second half-chamber; (b) a second bellows pump with a pump cavity bisected in coronal plane by a second elastomeric diaphragm, said second diaphragm dividing said pump cavity of said second bellows pump into a first half-chamber and a second half-chamber; (c) an aperture fluidly interconnecting said first half-chamber of said first bellows pump with said first half-chamber of said second bellows pump; (d) an inlet fluidly connected to said first half-chamber of said first bellows pump, wherein said inlet is comprised of a microfluidic channel with valve; (e) a pneumatic member pneumatically connected to said second half-chamber of said first bellows pump, wherein said pneumatic element is selected from the group consisting of a microchannel and a vent; and (f) a pneumatic member pneumatically connected to said second half-chamber of said second bellows pump, wherein said pneumatic element is selected from the group consisting of a microchannel and a vent.

In a further embodiment, the microfluidic cartridge further comprises dehydrated beads. In more specific embodiments, said dehydrated beads are affinity capture beads, such as paramagnetic beads or affinity capture beads having affinity for target analyte. Said target analyte may be selected from the group consisting of eukaryotic cell, bacterial cell, virus, macromolecule, antigen, antibody, epitope, nucleic acid, metabolite, small molecule, and drug. In other more specific embodiments, said affinity capture beads have affinity for a ligand. Said ligand may further comprise a member selected from the group consisting of eukaryotic cell, bacterial cell, virus, macromolecule, antigen, antibody, epitope, nucleic acid, metabolite, small molecule, and drug, or said ligand may further comprise a target analyte selected from the group consisting of eukaryotic cell, bacterial cell, virus, macromolecule, antigen, antibody, epitope, nucleic acid, metabolite, small molecule, and drug. In other more specific embodiments, said affinity capture beads have affinity for a nucleic acid or for an antigen.

In another further embodiment of the microfluidic cartridge, said pneumatic member connected to said second half-chamber of said first bellows pump is a microchannel and said pneumatic member connected to said second half-chamber of said second bellows pump is a vent.

In another further embodiment, the microfluidic cartridge further comprises molded members. Said molded members may comprise the walls of said aperture and bellows pump cavities.

In another embodiment, a kit is provided comprising the foregoing microfluidic cartridge, and further comprising a means for detecting a target analyte.

In another embodiment, a microfluidic apparatus for affinity capture is provided comprising: (a) a microfluidic cartridge comprising: (i) a first bellows pump configured for pumping a fluid sample:affinity capture bead suspension; (ii) a second bellows pump configured for pumping said sample:bead suspension; (iii) an aperture with depth, width and length fluidly interconnecting said first and second bellows pumps; (iv) an inlet with a microfluidic channel and a valve member, wherein said inlet is fluidly connected to said first bellows pump, and further wherein said microfluidic channel is configured for admitting a fluid sample and for opening and closing; and (v) a means for pneumatically actuating said bellows pumps, configured so that said sample:bead suspension is mixingly pumped back and forth through said aperture.

In a further embodiment, said aperture depth, width, and length are selected to effectively mix said sample:bead suspension.

In another further embodiment, the microfluidic apparatus further comprises a means for separating said affinity capture beads.

In another further embodiment, the microfluidic apparatus further comprises a means for detecting a target analyte.

In another further embodiment, said affinity capture beads are configured to capture a target analyte. Said target analyte may be selected from the group consisting of eukaryotic cell, bacterial cell, virus, macromolecule, antigen, antibody, epitope, nucleic acid, metabolite, small molecule, and drug.

In another further embodiment, said affinity capture beads are configured to capture a ligand. Said ligand may comprise a member selected from the group consisting of eukaryotic cell, bacterial cell, virus, macromolecule, antigen, antibody, epitope, nucleic acid, metabolite, small molecule, and drug or said ligand may further comprise a target analyte selected from the group consisting of eukaryotic cell, bacterial cell, virus, macromolecule, antigen, antibody, epitope, nucleic acid, metabolite, small molecule, and drug.

In another further embodiment, said affinity capture beads have affinity for a nucleic acid.

In another embodiment, a microfluidic apparatus for affinity capture is provided comprising: (a) a microfluidic cartridge comprising: (i) a first bellows pump configured for pumping a fluid:affinity capture bead suspension; (ii) a second bellows pump configured for pumping said fluid:bead suspension; (iii) an aperture with depth, width and length fluidly interconnecting said first and second bellows pumps, and configured for mixingly transporting said fluid:bead suspension between said first and second bellows pumps; and (iv) an inlet with a microfluidic channel and a valve member, wherein said inlet is fluidly connected to said first bellows pump, and further wherein said microfluidic channel is configured for admitting a fluid sample and for opening and closing; and (b) a pneumatic pulse generator and pneumatic distribution manifold, wherein said pulse generator is configured to deliver pneumatic pulses to said distribution manifold, and wherein said distribution manifold is engagedly connected to said microfluidic cartridge, and is configured to distribute said pneumatic pulses to at least one bellows pump, whereby said fluid:bead suspension is transported back and forth between said first and second bellows pumps when said valve member of said inlet is closed.

In a further embodiment, said aperture depth, width, and length are selected to effectively mix said sample:bead suspension.

In another further embodiment, said pneumatic pulses alternate between positive pressure and suction pressure.

In another further embodiment, said pneumatic pulses are directed in alternation to said first and second bellows pumps.

In another further embodiment, said pneumatic pulses further control said valve member.

In another further embodiment, the microfluidic apparatus further comprises a means for separating said affinity capture beads.

In another further embodiment, the microfluidic apparatus further comprises a means for detecting a target analyte.

In another further embodiment, said affinity capture beads are configured to capture a target analyte. Said target analyte may be selected from the group consisting of eukaryotic cell, bacterial cell, virus, macromolecule, antigen, antibody, epitope, nucleic acid, metabolite, small molecule, and drug.

In another further embodiment, said affinity capture beads are configured to capture a ligand. Said ligand may further comprise a member selected from the group consisting of eukaryotic cell, bacterial cell, virus, macromolecule, antigen, antibody, epitope, nucleic acid, metabolite, small molecule, and drug, or said ligand may further comprise a target analyte selected from the group consisting of eukaryotic cell, bacterial cell, virus, macromolecule, antigen, antibody, epitope, nucleic acid, metabolite, small molecule, and drug.

In another further embodiment, said affinity capture beads have affinity for a nucleic acid.

In another embodiment, a method for affinity capture of a ligand is provided, the method comprising: (a) admitting a fluid sample to a first bellows pump through a sample inlet having a microfluidic channel and a valve member; (b) adding affinity capture beads to said fluid sample; (c) closing said valve member; (d) pumping said fluid sample and said affinity capture beads back and forth through an aperture between said first bellows pump and a second bellows pump; (e) repeating step (d) until said sample and said beads are effectively mixed; (f) separating said beads and said sample; and (g) discharging said sample fluid and retaining said beads.

In another embodiment, a composition, apparatus, method or kit of the following disclosure is provided.

DETAILED DESCRIPTION OF SELECTED EMBODIMENTS

Figure 1A:
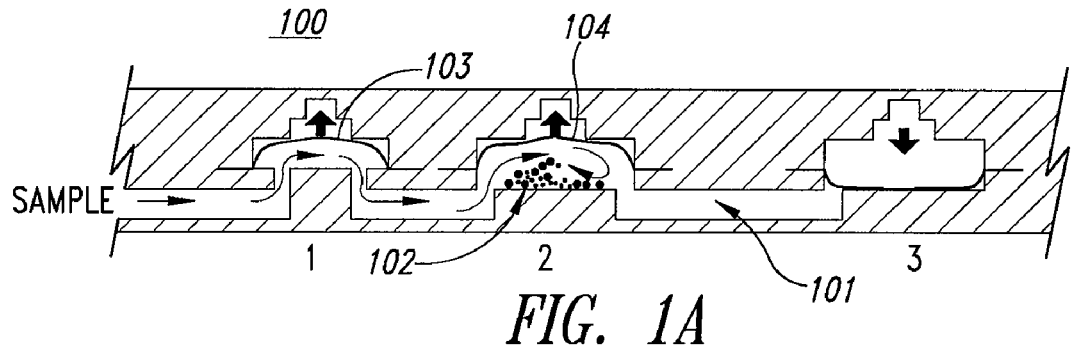
FIG. 1A-1D is a conceptual sketch of the operation of a paired bellows pump mixer, showing movement of a particle suspension during reciprocating flow.
Figure 1B:
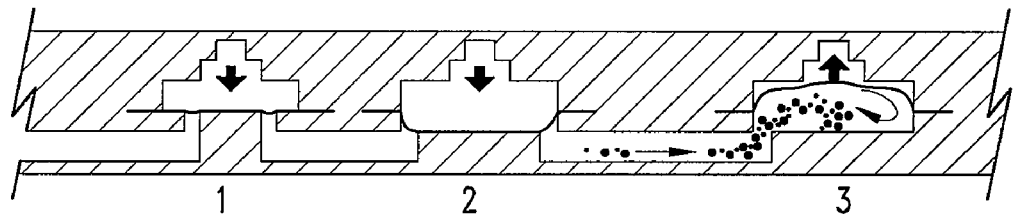
Figure 1C:
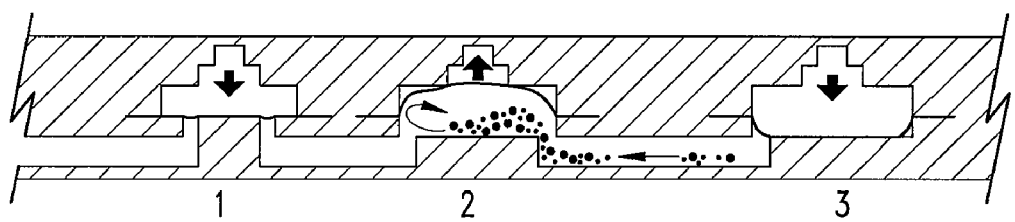
Figure 1D:
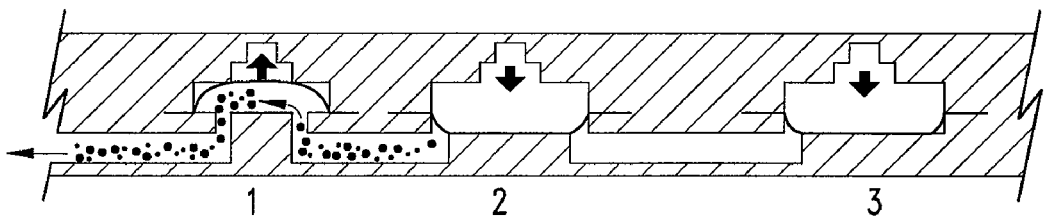

As an aid in better explaining the invention, the following definitions are provided. If any definition provided herein is inconsistent with a dictionary meaning, meaning as commonly understood in the art, or meaning as incorporated by reference to a patent or literature citation, the definition presented here shall prevail.

Definitions

Microfluidic cartridge: a "device", "card", or "chip" with fluidic structures and internal channels having microfluidic dimensions. These fluidic structures may include chambers, valves, vents, vias, pumps, inlets, nipples, and detection means, for example. Generally, microfluidic channels are fluid passages having at least one internal cross-sectional dimension that is less than about 500 μm and typically between about 0.1 μm and about 500 μm, but we extend the upper limit of the range to 600 um because the macroscopic character of the bead suspensions used here have a dramatic effect on the microfluidic flow regime, particularly as it relates to restrictions in the fluid path. Therefore, as defined herein, microfluidic channels are fluid passages having at least one internal cross-sectional dimension that is less than 600 um. The microfluidic flow regime is characterized by Poiseuille or "laminar" flow. The particle volume fraction (φ) and ratio of channel diameter to particle diameter (D/d) has a measurable effect on flow characteristics. (See for example, Staben M E et al. 2005. Particle transport in Poiseuille flow in narrow channels. Intl J Multiphase Flow 31:529-47, and references cited therein.)

Bellows Pump: is a device formed as a cavity, often cylindrical in shape, bisected in coronal section by an elastomeric diaphragm to form a first and a second half-chamber which are not fluidically connected. The diaphragm is controlled by a pneumatic pulse generator connected to the first half-chamber. Positive pressure above the diaphragm distends it, displacing the contents of the second half-chamber, negative gauge pressure (suction) retracts it, expanding the second half chamber and drawing fluid in. By half-chamber, it should be understood that the effective area of the diaphragm is the lesser of the volume displacement under positive pressure and the volume displacement under suction pressure, and it thus optimal when the first and second half chambers are roughly symmetrical or equal in volume above and below the diaphragm. The second half-chamber is connected to a fluid in-port and out-port. The fluid in-port and out-port may be separate ports or a single port, but in either case, are under valve control. As described above, a pneumatic pulse generator is pneumatically connected to the first half-chamber, generally by a microchannel, which is also valved. In the complete apparatus, pneumatic actuation is programmable. Thus, programmable pneumatic pressure logic used by the pulse generator has two functions, to actuate the diaphragm on signal, and to open and close valves on signal. When the pulse generator is off-cartridge, nipples or inlets, a pneumatic manifold and solenoid valves are provided.

In use, fluid enters the second half-chamber of a bellows pump through the inlet valve when negative pressure is applied to the diaphragm (or passively, when fluid is pushed in by a second bellows pump). Then, when positive pressure is applied to the diaphragm, the fluid contents of the chamber are displaced out through the outlet valve. Similarly, positive and negative pressure signals control valve opening and closing. By supplying a train of positive and negative pressure pulses to a diaphragm, fluid can be moved in and out of a bellows pump chamber. This fluid motion becomes directional by the application of synchronized valve logic, thus the pumping action.

As disclosed here, pairs of bellows pumps, i.e., "dual bellows pumps", can mix suspensions of beads or particles in fluids when configured with a first diaphragm pressure-actuated and a second diaphragm passive so as to force reciprocating flow between the two bellows chambers after the inlet and outlet valves are closed. Reciprocating flow can also be obtained by synchronously actuating both diaphragms with alternating or inverted pneumatic pulses. Similarly, a multiplicity of bellows pumps can be fluidly connected in series to perform a mixing function.

Test samples: Representative biological samples include, for example: blood, serum, plasma, buffy coat, saliva, wound exudates, pus, lung and other respiratory aspirates, nasal aspirates and washes, sinus drainage, bronchial lavage fluids, sputum, medial and inner ear aspirates, cyst aspirates, cerebral spinal fluid, stool, diarrhoeal fluid, urine, tears, mammary secretions, ovarian contents, ascites fluid, mucous, gastric fluid, gastrointestinal contents, urethral discharge, synovial fluid, peritoneal fluid, meconium, vaginal fluid or discharge, amniotic fluid, semen, penile discharge, or the like may be tested. Assay from swabs or lavages representative of mucosal secretions and epithelia are acceptable, for example mucosal swabs of the throat, tonsils, gingival, nasal passages, vagina, urethra, rectum, lower colon, and eyes, as are homogenates, lysates and digests of tissue specimens of all sorts. Mammalian cells are acceptable samples. Besides physiological fluids, samples of water, industrial discharges, food products, milk, air filtrates, and so forth are also test specimens. These include food, environmental and industrial samples. In some embodiments, test samples are placed directly in the device; in other embodiments, pre-analytical processing is contemplated. For example, fluidization of a generally solid sample is a process that can readily be accomplished off-cartridge.

Biomarker, target analyte, and ligand: a "biomarker" is a molecule or molecules for detection of a physiological condition of health or pathology in a vertebrate or cell, or for detection of a potential health-related condition in an environment. Biomarkers may include not only elements of the proteome, genome and metabolome of a vertebrate host or cell in health or disease, but also elements of the proteome, genome and metabolome of normal flora or pathogenic infectious agents, including bacterial, protozoan, and viral pathogens. Biomarkers include drugs, toxins and metabolites. Preferred biomarkers include DNA and RNA, and antigens and antibodies. Biomarkers include target analytes and also "ligands". As used herein, ligands are "handles" whereby a cell or molecule is affinity captured, and may also be a target analyte. However, ligands can also serve for indirect capture or concentrating of target analytes, or for removing or depleting interferences and inhibitors. A functional definition of "target analyte" is used here: target analytes are the biomarkers detected by a detection means.

Detection means: as used herein, "detection means" refers to device or apparatus for assessing and interpreting the result of an assay, which is generally the qualitative or quantitative detection of a target analyte. Detection endpoints are evaluated by an observer or a machine equipped with a spectrophotometer, fluorometer, luminometer, photomultiplier tube, photodiode, nephlometer, photon counter, electrodes, ammeter, voltmeter, capacitative sensors, radio-frequency transmitter, magnetoresistometer, or Hall-effect device. Particles, beads and microspheres, impregnated with a pigment or having a higher diffraction index, may be used to facilitate visual or machine-enhanced detection of an assay endpoint. Magnifying lenses in the cover plate, optical filters, colored fluids and labeling may be used to improve detection and interpretation of assay results. Detection of particles may be enhanced with "labels" or "tags" including, but are not limited to, dyes such as chromophores and fluorophores; radio frequency tags, plasmon resonance, or magnetic moment. Colloidal particles with unique chromogenic signatures depending on their self-association are also anticipated to provide detectable endpoints. Fluorescence quenching assays are anticipated. A variety of substrate and product chromophores associated with enzyme-linked immunoassays are also well known in the art and provide a means for amplifying a detection signal so as to improve the sensitivity of the assay. Molecular beacons are used similarly. Detection systems are optionally qualitative, quantitative or semi-quantitative.

The terms "tag", "label", or "marker" refer to a molecule or composition of molecules that is detectable by optical, spectroscopic, photochemical, biochemical, immunological, chemical or magnetic means, and is typically bound or complexed with a target analyte. Labels include, but are not limited to, colored, radioactive, fluorescent, ultraviolet, or magnetic molecules or particles conjugated to antibodies or other molecules or particles known to bind to cells or cellular components. Antibodies are often used as label components because of their ability to target specific cell types. Other reactive label components that can serve as alternatives to antibodies include, but are not limited to, genetic probes, dyes, fluorochromes, proteins, peptides, amino acids, sugars, polynucleotides, enzymes, coenzymes, cofactors, antibiotics, steroids, hormones or vitamins. The label often generates a measurable signal, which can be detected with or without some kind of stimulatory event and can be used to detect the presence of bound label and possibly quantitate the amount of bound label in a sample. Molecular beacons detect the state of hybridization of the beacon. Furthermore, the label may be a detectable intrinsic property of the cell, such as cell size or morphology, which is detectable, for example, by measuring light scattering characteristics. The label may be directly detectable or indirectly detectable or operate in conjunction with another label. (For further examples of labels see those listed in Handbook of Fluorescent Probes and Research Chemicals, Molecular Probes, Eugene, Oreg. hereby incorporated in full by reference.)

Reagent: refers broadly to any chemical or biochemical agent used in a reaction, including enzymes. A reagent can include a single agent which itself can be monitored (e.g., a substance that is monitored as it is heated) or a mixture of two or more agents. A reagent may be living (e.g., a cell) or non-living. Exemplary reagents for a nucleic acid amplification reaction include, but are not limited to, buffer, metal ion (for example magnesium salt), chelator, polymerase, primer, template, nucleotide triphosphate, label, dye, nuclease inhibitor, and the like. Reagents for enzyme reactions include, for example, substrates, chromogens, cofactors, coupling enzymes, buffer, metal ions, inhibitors and activators. Not all reagents are reactants, tags, or ligands, and no reagents are target analytes.

Via: A step in a microfluidic channel that provides a fluid pathway from one substrate layer to another substrate layer above or below, characteristic of laminated devices built from layers.

Air ports: refer to the arms of a pneumatic manifold under programmable control of external servomechanisms. The pneumatic manifold may be charged with positive or negative gauge pressure. Operating pressures of ±5 to 10 psig have been found to be satisfactory. Air and other gasses may be used.

Waste chamber or "waste pack": is a cavity or chamber that serves as a receptacle for sequestering discharged sample, rinse solution, and waste reagents. Typically also includes a wicking material (below). Waste packs may also be sealed under an elastic isolation membrane sealingly attached to the body of the microfluidic device. This inner membrane expands as the bibulous material expands, thus enclosing the waste material. The cavity outside the isolation membrane is vented to atmosphere so that the waste material is contained and isolated. Waste packs may optionally contain dried or liquid sterilants.

Wick: is a bibulous material used to propulse fluid flow by capillary wetting in place of, or in concert with, microfluidic pumps. The bibulous core typically includes a fibrous web of natural or synthetic fibers, and also often includes certain absorbent gelling materials usually referred to as "hydrogels," "superabsorbent" or "hydrocolloid" materials. Materials include papers, sponges, diaper materials, Contec-Wipe, and others. Dessicants may also be used, such as calcium sulfate, calcium sulfate, silica gel, alone or in combination with bibulous materials. Other materials include papers, sponges, diaper materials, Contec-Wipe™ (Contec, Spartanburg S.C. USA), for example.

Vent: a pore intercommunicating between an internal cavity and the atmosphere. A "sanitary" or "isolation vent" also contains a filter element that is permeable to gas, but is hydrophobic and resists wetting. Optionally these filter elements have pore diameters of 0.45 microns or less. These filters function both in forward and reverse isolation. Filter elements of this type and construction may also be placed internally, for example to isolate a valve or bellows pump from the pneumatic manifold controlling it. An example is Mupor™ a porous PFTE composition available from Porex Porous Products Group (Fairburn Ga. USA).

Herein, where a "means for a function" is described, it should be understood that the scope of the invention is not limited to the mode or modes illustrated in the drawings alone, but also encompasses all means for performing the function that are described in this specification, and all other means commonly known in the art at the time of filing. A "prior art means" encompasses all means for performing the function as are known to one skilled in the art at the time of filing, including the cumulative knowledge in the art cited herein by reference to a few examples.

Means for affinity capturing: refers to an incorporated element of a device or apparatus, commonly termed a bead, particle, microsphere, for capturing ligands from a test sample, and includes not only the examples provided here, but also the cumulative knowledge in the art at the time of filing. Capture is based on hydrogen bonding, hydrophobic bonding, and Van der Waal's forces, and is influenced by salt and solute concentrations, zeta potential, dielectric constant of the solvent, temperature, cooperative binding, and the like. Under certain reaction conditions, capture may be covalent, such as in the interaction of metal chelates with histidine.

Means for separating affinity capture beads: refers to various separation methods, including magnetic capture, second ligand affinity capture as in solid phase immobilization, centrifugation or sedimentation, filtration, and field flow fractionation. These are bead separation means as used herein.

Beads: is used to refer to particles, nanoparticles or microspheres, and may be made of a paramagnetic material, superparamagnetic material, a latex, polymer, ceramic, silicate, gel or a composite of such, and may contain layers. Beads are classified here on the basis of size as large (1.5 to about 50 microns), small (0.7-1.5 microns), or colloidal (<200 nm), which are also referred to as nanoparticles. Beads are generally derivatized for use in affinity capture of ligands, but some beads have native affinity based on charge, dipole, Van der Waal's forces or hydrophobicity. Hundreds or many thousands of beads at time are generally used in affinity capture.

Means for detecting: as used herein, refers to a device for assessing and displaying an endpoint, i.e., the result of an assay, and may include a detection channel and test pads. Detection endpoints are evaluated by an observer visually in a test field, or by a machine equipped with a spectrophotometer, fluorometer, luminometer, photomultiplier tube, photodiode, nephlometer, photon counter, voltmeter, ammeter, pH meter, capacitive sensor, radio-frequency transmitter, magnetoresistometer, or Hall-effect device. Particles, beads and microspheres, impregnated with color or having a higher diffraction index, may be used to facilitate visual or machine-enhanced detection of an assay endpoint. Magnifying lenses in the cover plate, optical filters, colored fluids and labeling may be used to improve detection and interpretation of assay results. Means for detection of particles, beads and microspheres may include "labels" or "tags" such as, but not limited to, dyes such as chromophores and fluorophores; radio frequency tags, plasmon resonance, or magnetic moment as are known in the prior art. Colloidal particles with unique chromogenic signatures depending on their self-association are also anticipated to provide detectable endpoints. QDots, such as CdSe coated with ZnS, decorated on magnetic beads, or amalgamations of QDots and paramagnetic $Fe_3O_4$ microparticles, optionally in a sol gel microparticulate matrix or prepared in a reverse emulsion, are a convenient method of improving the sensitivity of an assay of the present invention, thereby permitting smaller test pads and larger arrays. Fluorescence quenching assays are anticipated. A variety of substrate and product chromophores associated with enzyme-linked immunoassays are also well known in the art and provide a means for amplifying a detection signal so as to improve the sensitivity of the assay. Molecular beads are used similarly. Detection systems are optionally qualitative, quantitative or semi-quantitative.

"Conventional" is a term designating that which is known in the prior art to which this invention relates, particularly that which relates to electric guitars.

"About", "generally", and "roughly" are broadening expressions of inexactitude, describing a condition of being "more or less", approximately, or almost, where variations would be obvious, insignificant, or of lesser or equivalent utility or function, and further indicating the existence of obvious exceptions to a norm, rule or limit.

DETAILED DESCRIPTION OF THE FIGURES

As noted previously, the present invention relates to microfluidic devices, apparatuses, and methods utilizing a plurality of microfluidic channels, inlets, valves, membranes, pumps, liquid barriers and other elements arranged in various configurations to manipulate the flow of a fluid sample in order to prepare such sample for analysis and to analyze the fluid sample. In the following description, certain specific embodiments of the present devices and methods are set forth, however, persons skilled in the art will understand that the various embodiments and elements described below may be combined or modified without deviating from the spirit and scope of the invention.

FIG. 1 shows the basic elements of a simple mixing process. The mixing device 100 has, from left to right, a single valve at 1, a bellows pump at 2, and a second bellows pump at 3. The lower bellows chambers are fluidly interconnected by an aperture 101. In this embodiment, a dry pill 102 of affinity capture beads (dark circles) was placed in the first bellows pump during manufacture. While the construction will be described in more detail below, the actions of the device are described here.

In Step 1, fluid sample is shown entering through an intake channel from the left. Suction pressure (indicated by the solid up arrow top of chamber) opens the diaphragm 103 of valve 1 and also lifts the diaphragm 104 in the bellows chamber at 2, drawing the fluid into the device. As fluid contacts the bead pill, hydrated beads are released into the fluid, forming an agitated suspension.

In Step 2 (FIG. 1B), valve 1 is closed, and suction pressure above the diaphragm in bellows pump at 3 pulls down the diaphragm in bellows pump at 2 and pulls the fluid from chamber 2 to chamber 3, with limited dead volume. While in the aperture, fluid flow is laminar. However, upon entry into chamber 3, the inertia of the bead stream promotes mixing and molecular collisions needed to contact the affinity capture beads and a soluble target ligand or target analyte, as the case might be.

In Step 3 (FIG. 1C), valve 1 remains closed so that the fluid action is confined to the two bellows pumps at 2 and 3. By reversing suction pressure, applying it here to the bellows chamber 2, the fluid bolus is pulled out of chamber 3 and returned to chamber 2. Again, fluid flow in the aperture is laminar, but upon entry into chamber 2, the inertia of the bead stream promotes mixing and molecular collisions need to further contact the affinity capture beads and any soluble target ligand or target analyte in solution.

Note that Steps 2 and 3 can be repeated for any number of cycles simply by alternating suction pressure between the two bellows pumps. While not shown here, pressure in the bellows pumps can be alternated between positive and suction pressure, again resulting in reciprocating flow of the fluid bolus. Alternatively, a single bellows pump, for example at 3, can be actively toggled between positive and suction pressure, while the bellows pump at 2 follows passively, but again the result is reciprocating flow. These options are indicated by the up and down arrows in the chambers, and it should be obvious following this explanation that various permutations are possible.

In step 4 (FIG. 1D), valve 1 is again open. The mixed bead suspension and sample fluid can now be expelled from the mixing device. This can be performed by applying positive pressure to bellows pumps at 2 and 3, or by applying suction pressure to the intake channel externally of the mixing device. Because of the compliance of the elastomeric membranes, sample hold up approaches zero dead volume.

Note that the bead suspension need not exit via the intake port. By providing a second valved port to the right of chamber 3, it is possible to exit the fluid from left to right. Although not shown here, embodiments described below will show this alternate configuration.

Figure 2:
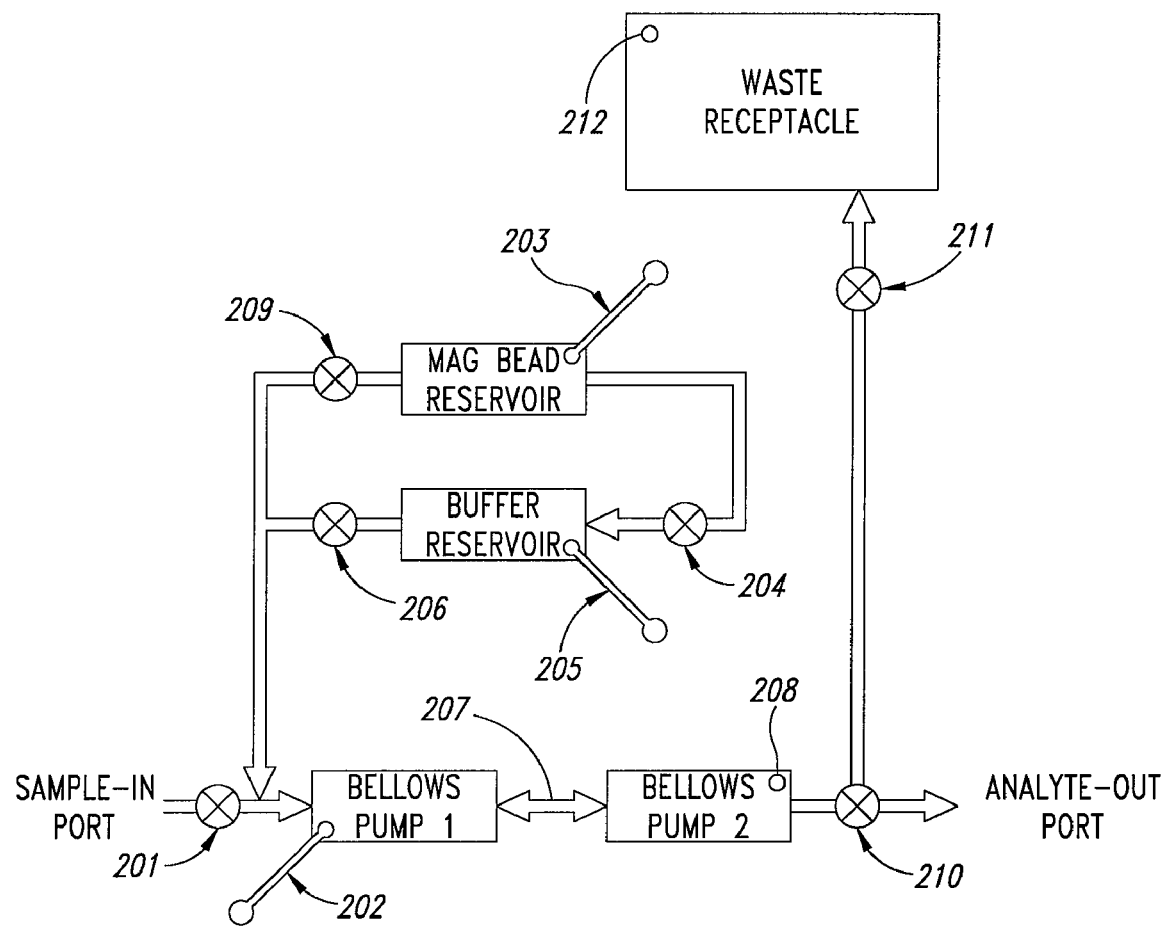
FIG. 2 is a conceptual sketch of the operation of a simple microfluidic cartridge incorporating the mixing device of FIG. 1. Sample fluidization and data collection is performed off-cartridge.

Turning to FIG. 2, a simplified but representative microfluidic mixing and analyte capture apparatus is illustrated schematically. Sample is pipetted into the apparatus via the sample in port, through valve 201 and into bellows pump 1. The pneumatic actuator 202 or "air port" serves to draw the sample into the bellows chamber. All valves in the apparatus are then closed. Note that all valves, illustrated with the crossed circle, are pneumatic valves, but this should not be construed as a limitation on the invention. Using only pneumatic actuator 202, both bellows pump 1 and bellows pump 2 can be controlled. Both pumps are configured with elastomeric diaphragms contacted with the fluid so that pressure pulses delivered to one side of the diaphragm move the fluid on the other side. Diaphragm material is selected for its compliance, so that the diaphragm displaces essentially all of the fluid in the chamber when pressurized.

As discussed in the first figure, which detailed the action of the bellows pump mixing device, upon entry into the first bellows pump, the sample is mixed with affinity capture beads. Here, instead of a dry pill in the bellows pump chamber, the beads are pre-assembled in a dry matrix in the mag bead reservoir and are rehydrated with buffer before use. Application of pneumatic pressure at air port 203, and opening valve 204, dispenses buffer into the mag bead reservoir. Application of pneumatic pressure at air port 205, and opening valve 206, dispenses the mag bead suspension into the fluid chamber of bellows pump 1, which also contains the sample. All valves are again closed.

Pneumatic actuator 202 then forces the sample-bead suspension into bellows pump 2 through aperture 207. This process is reversed by reversing the pressure at 202 from positive to negative. Suction pressure pulls the bead suspension out of bellows pump 2 and returns it to bellows pump 1. The process is repeated until the sample and affinity capture beads are fully reacted. Note that the pneumatic chamber of bellows pump 2, which behaves passively, is vented at 208.

Upon completion of the affinity capture reaction, the beads are rinsed with buffer to remove inhibitors, interferences, and sample matrix. This can be readily accomplished with magnetic beads, for example. Preparation of monodisperse beads with a paramagnetic core and a coat of an antibody, antigen, avidin, nucleic acid oligomer, nickel chelate, ion exchange polymer, or other affinity capture molecule, is well known in the art. To capture magnetic beads during washing, the beads are simply held in place with a magnet held above or below the bellows pump chambers containing them. Wash buffer may then be introduced by actuating the buffer reservoir at air port 203 and opening valve 209. All valves are then closed, and by actuating bellows pump 1 with pulses of positive and negative pressure, the wash fluid can be caused to flow back and forth between the two bellows chambers, washing the magnetically immobilized beads. Spent wash fluid is discharged to the waste receptacle by opening valves 210 and 211. The waste receptacle is vented, and generally contains an absorbent material that wicks up the fluid. All valves are then closed and the wash process is repeated as necessary.

After the wash process is completed, the apparatus is then reconfigured by closing all valves, then dispensing a small amount of buffer into bellows pump 1, transferring it to bellows pump 2, where the beads are held in place magnetically. Upon release of the magnet, the beads are readily resuspended with mixing, and are finally discharged by opening valve 210 and collecting them at the analyte out port, whereupon any analyte captured may be subjected to further analysis. Affinity ligand capture may also be used to remove undesired inhibitors or interferences from a sample.

Figure 3:
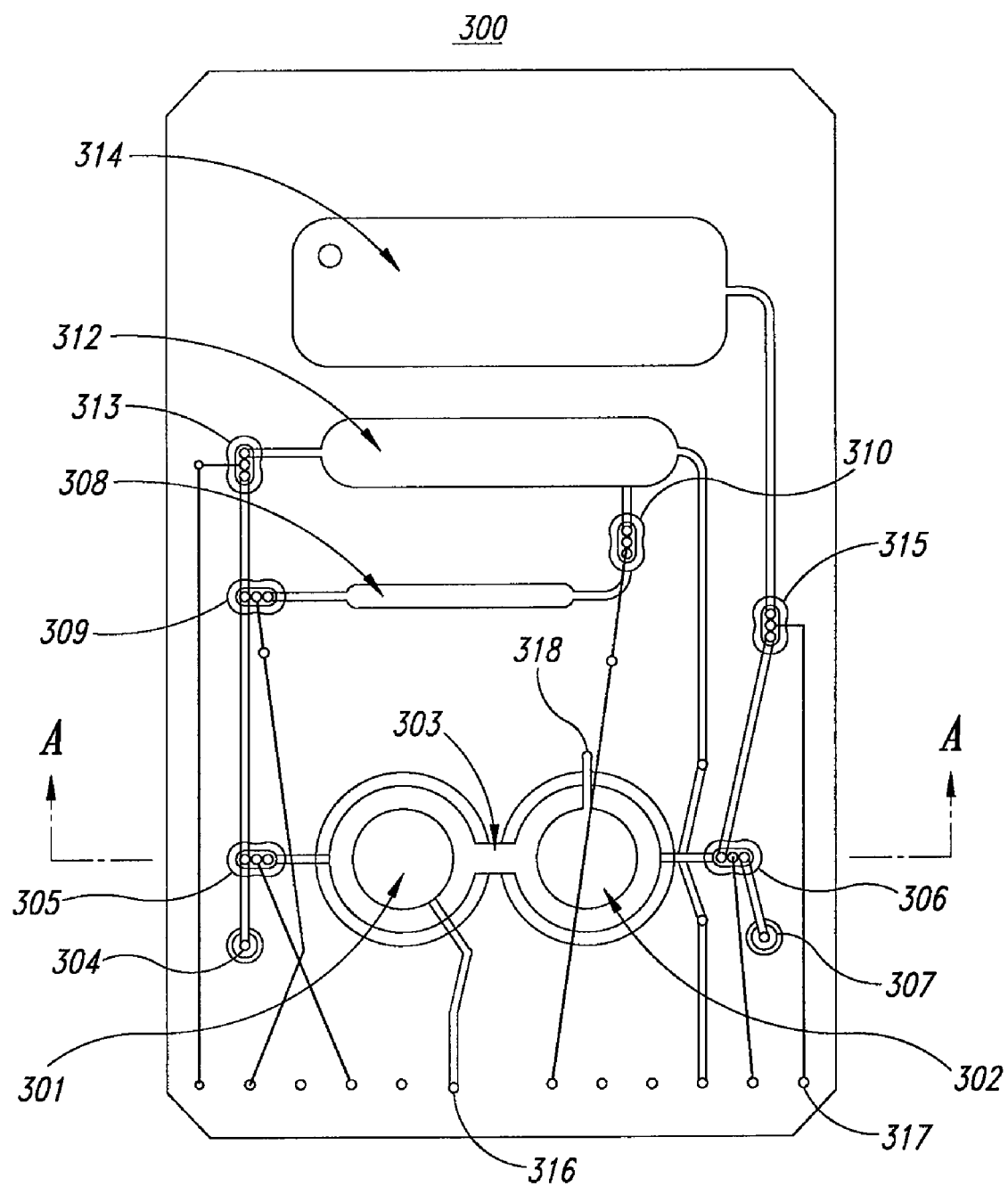
FIG. 3 is plan view of the microfluidic cartridge of FIG. 3, as was created for assay development. Shown is the cross-sectional cut taken for FIGS. 4 and 5.

FIG. 3 is an engineering layout of a microfluidic cartridge of the design of FIG. 2. Microchannels that appear to intersect improperly are laid out at different depths in the solid body of the cartridge. Nonetheless, the function of the card closely follows that of FIG. 2.

Shown are bellows pump 1 (301) and bellows pump 2 (302), fluidly interconnected by microchannel 303. Valves 305 and 306 control fluid entry from the sample-in port 304 and to the analyte-out port 307, respectively. Pneumatic actuation channels controlling these valves can be followed to an off-cartridge port at the base of the cartridge device. Similarly, air port 316 controls the diaphragm of first bellows chamber 301, and air port 317 controls valve 315 which accesses waste receptacle 314.

Thus the microfluidic cartridge shown here is integrated into a larger apparatus which includes a pneumatic pulse generator and controller (not shown). A total of 12 pneumatic control lines originating at the bottom of the cartridge, of which 8 are used and 4 are not used, are available in this design.

Sample enters the first bellows chamber 301 through valve 305 from inlet port 304. Affinity capture beads are rehydrated in bead reservoir 308 with buffer from buffer reservoir 312 via valve 310. Valve 309 and 305 are opened to add the bead suspension to the sample. The bead-sample suspension is then forced through aperture 303 into passive bellows pump 302, the pneumatic chamber of which is vented at 318. By applying suction pressure through air port 316, the diaphragm of bellows pump 301 can be retracted, thus drawing the bead-sample suspension back through aperture 303. This process is repeated until the affinity capture beads and sample are fully reacted.

Wash buffer from reservoir 312 is dispensed into the bellows pump mixer via valves 313 and 305. Beads are rinsed and the waste fluid is expelled from bellows chamber 302 via valved line 315 to waste receptacle 314. When wash is completed, beads are collected and recovered through valve 306 in analyte-out port 307. Further analysis is performed off-cartridge. However, the microfluidic device is part of an apparatus for performing a method. As will be shown below, analytical detection means structures can also be integrated on-cartridge. This could also be considered a process, for example for the purification of viable stem cells, and we have disclosed optional sanitary features elsewhere.

To better visualize the paired bellows pump mixer, a section taken at A-A on the cartridge of FIG. 3 is shown in FIGS.

Figure 4:
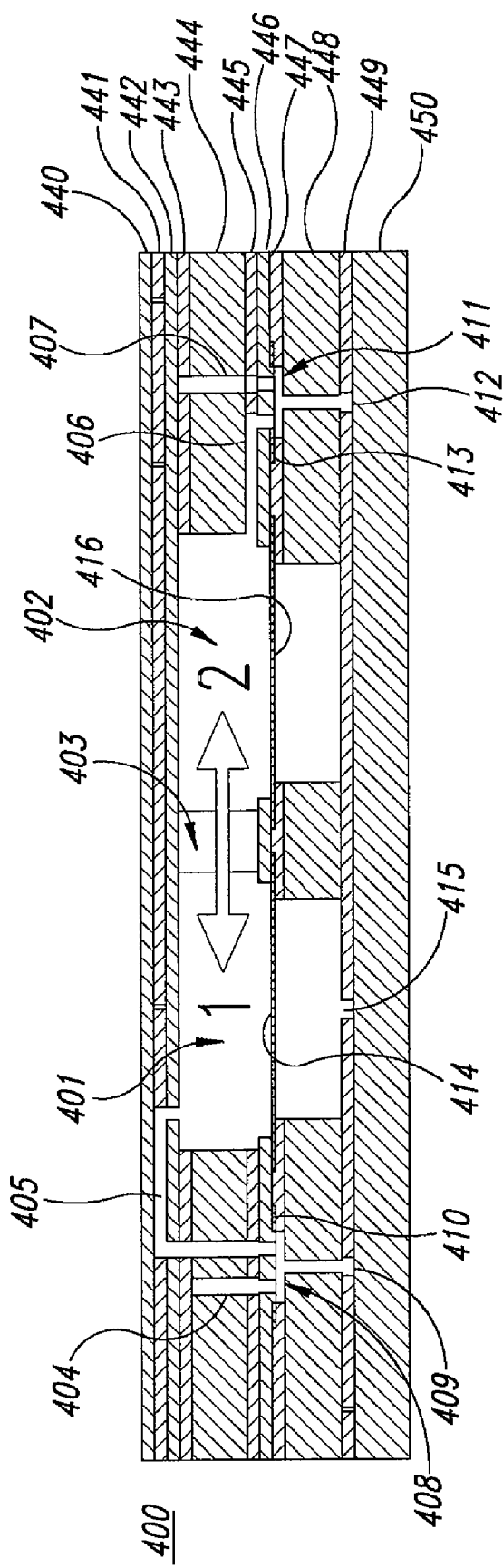
FIG. 4 is a cross-section through the paired bellows pumps of the microfluidic device of FIG. 3 as fabricated by lamination.
Figure 5:
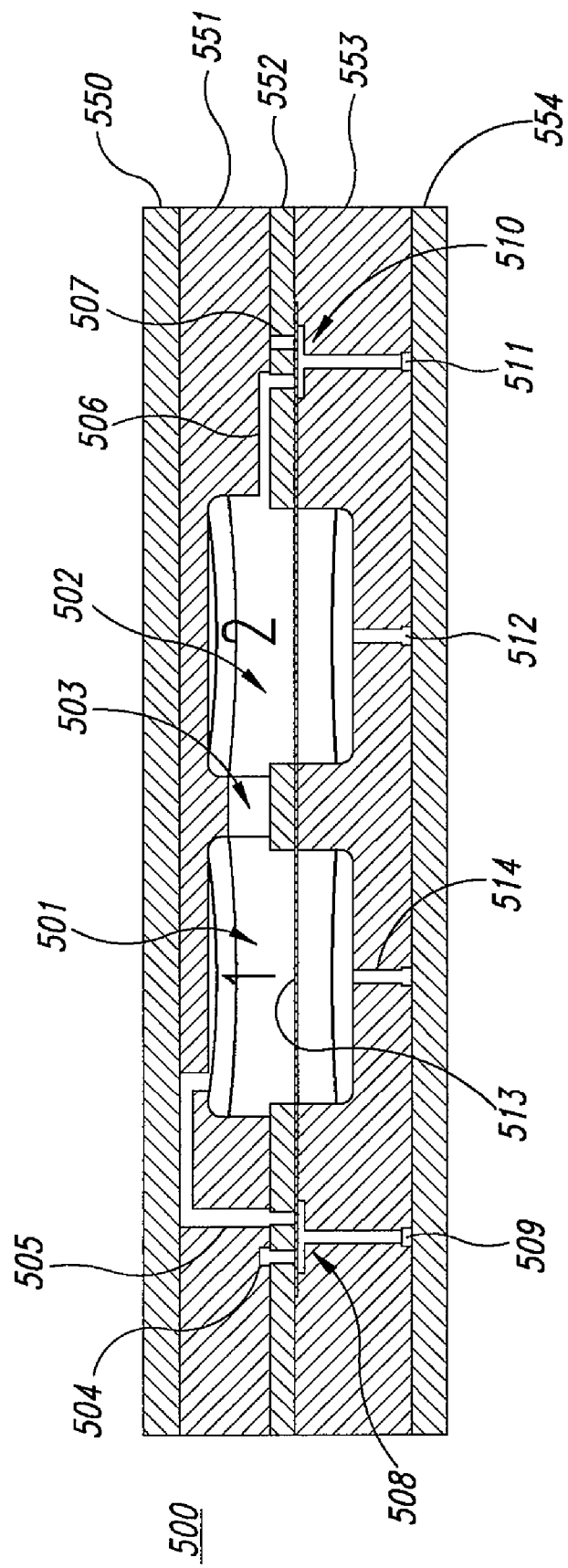
FIG. 5 is a cross-section through the paired bellows pumps of a microfluidic device of FIG. 3 as fabricated with injection molding.

4 and 5. FIG. 4 assumes construction with laminated layers. FIG. 5 has elements of an injection molded cartridge.

Turning to FIG. 4, a cross-section through the device of FIG. 3 at A-A, we show a cartridge fabricated by lamination of multiple layers. This embodiment requires 6 layers of solid plastic laminated together by 5 layers of a double-sided adhesive on a thin plastic core (ACA). The adhesive layers have thickness and can be used to route microchannel extensions from the off-cartridge pneumatic manifold. In this section as drawn, the thickness of the layers is not representative of an actual device, which may be only $1/5^{th}$ of an inch in total thickness, or less.

FIG. 4 is a representation of a cross-section through the cartridge of FIG. 3 at A-A. The construction is laminated, and the thicknesses of the layers are exaggerated for clarity. Two bellows pumps are shown, numbered in bold, "1" and "2". As before, each bellows pump consists of an upper and lower chamber separated by an elastomeric diaphragm. The double arrow between the upper chambers indicates fluid flow during the mixing step.

The functional elements are as follows. Sample entry is through channel 404 and valve 408. Sample continues into the upper chamber 401 of bellows pump 1 through channel 405. Note that in this embodiment, the fluid is on top of diaphragm 414, not beneath it as in FIG. 1. Beads are thus directly agitated by the physical motion of the diaphragm as well as by the liquid motion, and in the case of magnetic beads, may conveniently be held against the roof of the chamber with a magnet during washes. Valve control is achieved through air port 409, which displaces valve diaphragm 410. Note the "tee" shaped structure of the valve cavity. It can be seen that in the closed position (as shown), the valve diaphragm 410 impinges the vias in the upper layer, effectively preventing flow from channel 404 to 405. Under suction pressure, the diaphragm is drawn away from the channel orifices, allowing flow through the valve.

Bead suspension enters the mixing device through channels 404 and 405, and beads and sample commingle in bellows pump 1 before being forced into bellows pump 2. Note that bellows diaphragm 414 is controlled by air port 415. The second bellows diaphragm 416 contacting the fluid in bellows chamber 402 follows the opposing motions of diaphragm 414 passively. When diaphragm 414 goes up, diaphragm 416 is displaced down, and fluid moves from bellows pump 1 to bellows pump 2 through aperture 403. This process is then reversed and then continued with reciprocating flow until the affinity capture reaction is completed.

Wash reagent also enters the mixing device through channels 404 and 405. During the wash step, the sample:bead suspension is again moved back and forth between chambers 401 and 402.

Upon completion of the wash step, or steps, the sample:bead suspension is separated, and the unwanted fluid is discharged through channels 406 and 407, under the control of valve 411, which again has microfluidic structure (air port 412 and diaphragm 413). The beads may then be resuspended in fresh buffer and collected through channels 406 and 407.

We supply an overview of the materials of construction so as to show how obvious substitutions can be made to a laminated cartridge design. Layers 441, 443, 445, 447, and 449 are ACA cores—double-sided adhesive layers, with a core of PET (polyethylene terephthalate). Layers 440 and 450 are outer shell layers and are often made of polyacrylate plastic. Layer 442 is made here of PMMA (polymethmethacrylate). Layers 444 and 448, which form the walls of the upper and lower bellows pump chambers, are often made of PET and may be about $1/16$ inch thick for typical sample volumes envisaged in this embodiment. Layer 447 is a complex layer, because it contains the elastomeric membrane insert. Polyurethane or polysilane and other elastomeric inserts have been fabricated successfully, typically on a PET basement layer, which is then inserted into the layer stack as a separate assembly. The knowledge to select other plastics or solid substrates is widely known in related arts.

Turning now to FIG. 5, the engineering design is again based on FIG. 3. However, injection molded elements are substituted, so that the total number of laminated layers is only 5. With this construction, it is also possible to apply a radius to the bellows chambers and to selected channels. Note also that the elastomeric layer 513 serves as a single-piece diaphragm spanning the two bellows pumps 1 and 2 and the two valves 508 and 510.

More briefly, the operation is essentially that of FIGS. 3 and 4. Fluid and beads enter bellows chamber 501 through channels 504 and 505, and valve 508 is then closed by the action of air port 509. Diaphragm 513 in the first bellows chamber is then actuated with air port 514, forcing the sample:bead suspension into diaphragm pump 2. Mixing action is obtained by forcing the suspension through aperture 503. The actions are then reversed so as to generate reciprocating flow, which is continued until the affinity capture reaction is completed. Wash buffer may be added through channel 504 from an on-cartridge reagent reservoir. After washing, excess fluid is discarded through channels 506 and 507 under the control of valve 510 and air port 511. Discarded wash fluid is sequestered on-cartridge. Channel 507 also serves to port the final bead concentrate to a collection point for further analysis. Further analysis may be performed on-cartridge or off-cartridge, depending on the degree of integration in the microfluidic cartridge.

As before, the apparatus also comprises a pneumatic manifold and pneumatic pulse generator, with microprocessor-based control of the valve logic and diaphragm actuation. These features are not shown, and are handled by an apparatus into which the microfluidic cartridge is placed. Hand-held and semi-automated embodiments have also been constructed.

Materials components of the molded card are as follows: Layers 550 and 554 are cap layers, typically of PET. Layers 551 and 553 are PMMA. Layer 553 has been prefabricated with a polyurethane membrane (513) on its upper surface. Layer 552 is made of PET. All shaping not accomplished in the mold design is completed by laser cutting. Obvious variations and substitutions are contemplated.

Figure 6:
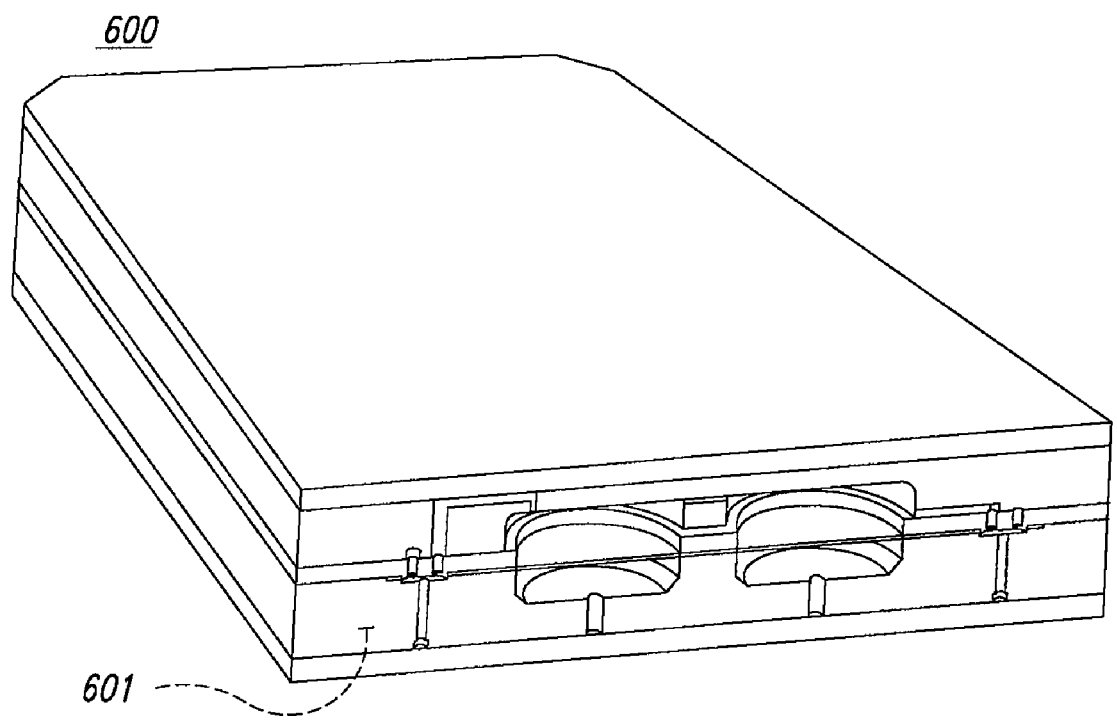
FIG. 6 is an isometric view, with perspective, of the microfluidic device of FIG. 5.

In FIG. 6, the device 600 is presented as a 3-dimensional CAD rendering with perspective. The same A-A cross-section is taken as was described in FIG. 3. On the plane of the section 601, the device is shown to contain two bellows pumps fluidly interconnected by an aperture. Microfluidic channels and valves for introducing sample and collecting analyte are also provided.

In one embodiment, herein is provided a microfluidic cartridge for mixing a sample and a bead suspension so as to promote affinity capture. The cartridge has a first bellows pump with pump cavity bisected in coronal plane by a first elastomeric diaphragm, the first diaphragm dividing the pump cavity thereof into a first half-chamber and a second half-chamber; a second bellows pump with pump cavity bisected in coronal plane by a second elastomeric diaphragm, the first diaphragm dividing said pump cavity thereof into a first half-chamber and a second half-chamber; an aperture fluidly interconnecting the two fluid chambers; a sample inlet and inlet valve fluidly connected to the first half-chamber of said first bellows pump; a pneumatic member pneumatically connected to the second half-chamber of the first bellows pump, wherein the pneumatic element either a microchannel or a vent; and, a pneumatic channel pneumatically connected to the second half-chamber of said second bellows pump, wherein the pneumatic element is either a microchannel or a vent. In an operative configuration, one bellows pump will be actuated by a pneumatic pulse delivered through a pneumatic microchannel. The second bellows pump may be vented and operated passively, or may also be activated by a second pneumatic pulse delivered through a pneumatic microchannel, the pulses delivered to the two bellows pumps being either alternating positive pressure pulses, alternating negative pressure pulses, or opposite in sign, taking gauge pressure at atmosphere as zero.

These cartridges can be microfabricated using a variety of methods, including without limitation, traditional lithographic techniques, soft lithography, laminate technologies, polymer molding, etc. For example, the cartridge can be microfabricated from any etchable, machinable or moldable substrate. The term machining as used herein includes, without limitation printing, stamping cutting and laser ablating. The cartridge can be formed in a single sheet, in a pair of sheets sandwiched together, or in a plurality of sheets laminated together. The term "sheet" refers to any solid substrate, flexible or otherwise. Optionally, fluidic channels in the cartridge can be etched in a silicon substrate and covered with a cover sheet, which can be a transparent cover sheet. In a laminated embodiment, fluidic channel walls are defined by removing material from at least one sheet, thus creating channels and voids, and positioning additional sheets on either side of the altered sheets. Any of the layers can contain fluidic channels. In some cases the channel is simply a hole (or fluid via) to route fluid to the next laminate layer. Any two adjacent laminate layers may be bonded together to form a more complex element.

In some embodiments, the microfluidic cartridges of the invention contain molded members, and these molded members may be used to form the bowl and channel cavities that form the bellows pump, aperture, and supporting microfluidic elements.

In some embodiments, microfluidic cartridges are pre-assembled with dehydrated affinity capture beads. These beads may be affinity capture beads, or beads adapted for sample comminution. In one preferred embodiment, the beads are paramagnetic or superparamagnetic beads. Affinity capture beads have affinity for target analyte, or more generally, for a ligand. Target analytes include eukaryotic cells, bacterial cells, viruses, macromolecules, antigens, antibodies, epitopes, nucleic acids, metabolites, small molecules, and drug. Target analytes are a subset of ligands, which are either target analytes or are a "handle" that is attached to an eukaryotic cell, bacterial cell, virus, macromolecule, antigen, antibody, epitope, nucleic acid, metabolite, small molecule, or drug. Of recent interest are affinity capture beads have affinity for a nucleic acid and affinity capture beads having affinity for an antigen. Beads of these sorts are useful as part of the inventive devices, and may be added during operation, or assembled in the cartridge in dehydrated form during manufacture. In this way, useful kits can be made which contain microfluidic cartridges with the dual bellows pump mixer and affinity capture beads. In some instances, only sample need be added by the user.

In yet another embodiment, a microfluidic apparatus is provided. The apparatus is a microfluidic cartridge which contains, or to which is added, the affinity capture beads. The microfluidic cartridges are designed with dual bellows pump mixers on-cartridge. The aperture in these mixers is configured to optimize mixing or comminution of the sample:bead suspension, and a means is provided for pneumatically actuating the bellows pumps so that said sample:bead suspension is mixingly pumped back and forth through the aperture. The means may include hand pressure, semi-automated actuators, or a fully automated actuator with pneumatic pulse generator and pneumatic distribution manifold. The pulse generator is configured to deliver pneumatic pulses to the distribution manifold and the microfluidic cartridge is plugged in to the distribution method or otherwise connected or engaged with it. The pneumatic pulses are transmitted through microchannels to the pumps and valves. By actuating the pump diaphragms, the fluid:bead suspension can be transported back and forth through the aperture, but any valves in and out of the dual bellows pump mixer must first be closed. Automated, semi-automated, and manual methods for opening and closing valves in the proper order are anticipated. In the automated form, microprocessor-controlled solenoids control the pneumatic pulses in the proper sequence.

In some embodiments, microfluidic apparatuses of the invention also contain a means for separating said affinity capture beads, or may contain a means for detecting a target analyte. Target analytes include eukaryotic cells, bacterial cells, viruses, macromolecules, antigens, antibodies, epitopes, nucleic acids, metabolites, small molecules, and drugs. Target analytes are a subset of ligands, which are either target analytes or are a "handle" that is attached to an eukaryotic cell, bacterial cell, virus, macromolecule, antigen, antibody, epitope, nucleic acid, metabolite, small molecule, or drug. Of recent interest are affinity capture beads have affinity for a nucleic acid and affinity capture beads having affinity for an antigen. Beads of these sorts are useful as part of the inventive apparatuses, and may be added during operation, or assembled in the apparatus in dehydrated form during manufacture. Of particular interest are apparatuses for the capture of nucleic acids and antibodies from blood and other test specimens.

The above devices and apparatuses are further configured for use with affinity capture beads. Analytical methods employing the devices and apparatuses are further contemplated. Capture and isolation methods for live cells, such as stem cells, are also anticipated.

We teach here methods for configuring a cartridge or apparatus and the requisite aperture for the intended application. Parameters such as aperture dimensions, actuation pressure, pulse shape, bellows chamber diameter (as "effective diameter), can be varied to adjust mixing and shear forces for particular samples and applications, pulse frequency and duration of mixing.

Figure 7A:
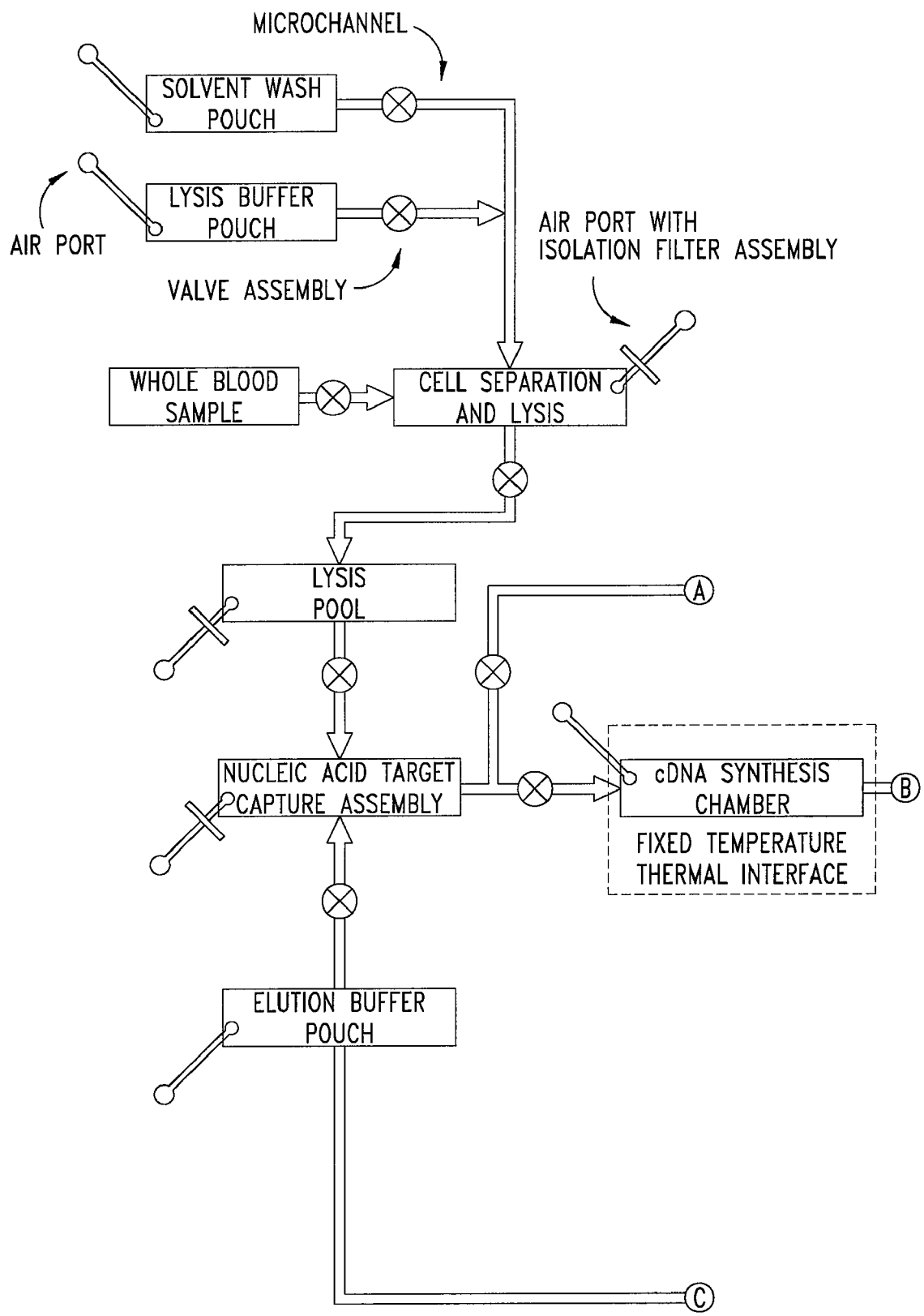
FIGS. 7A and 7B is a schematic of a microfluidic apparatus with paired bellows pump mixers and integrated detection means. The off-cartridge pneumatic manifold and control circuit is not shown.
Figure 7B:
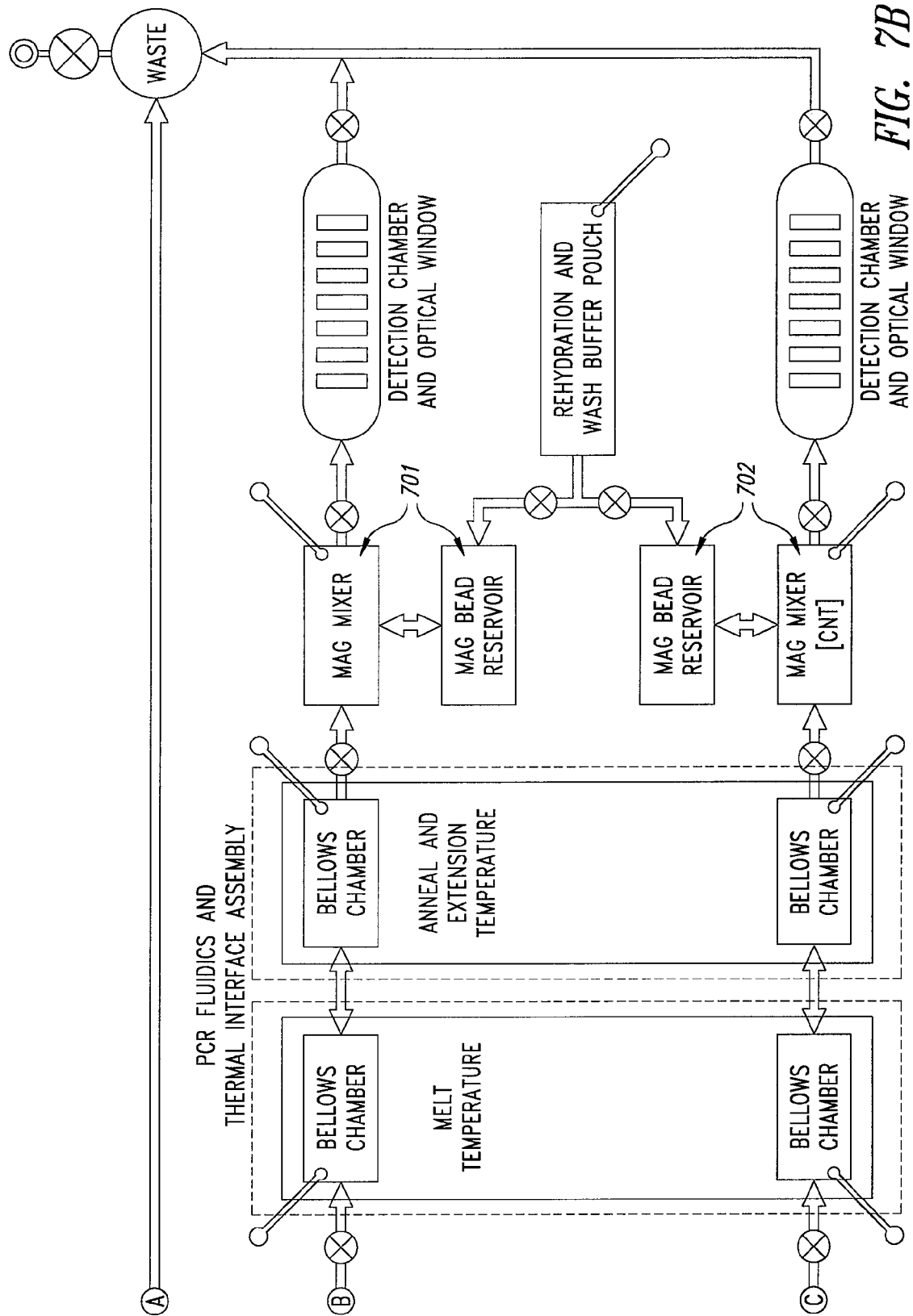

Higher integrations are also contemplated. In FIG. 7, two dual bellows pump mixers (701, 702) are shown as part of an integrated analytical circuit with PCR amplification and amplicon detection means. Magnetic beads are mixed with the PCR reaction mixture. The beads have been previously coated with oligomer so as to capture complementary cDNA sequences. Means for bead separation involve subsequent capture of the beads, which are optionally tagged, on a suitable solid substrate, such as a test pad. Beads are optionally magnetic. Suitable beads also include latex beads derivatized as described by Wolf (see Wolf S F et al. 1987. Rapid hybridization kinetics of DNA attached to submicron latex particles. Nucl Acids Res 15:2911-2926) and more recently by Fuentes (see Fuentes M et al. 2006. Detecting minimal traces of DNA using DNA covalently attached to superparamagnetic nanoparticles and direct PCR-ELISA. Biosensors Bioelectronics. 21:1574-1580). In the latter study, longer linkers were synthesized, permitting primer extension directly on the magnetic beads. Integration of this kind of nucleic acids technology into microfluidic devices and apparatuses is fully contemplated within the scope of this invention.

Figure 8:
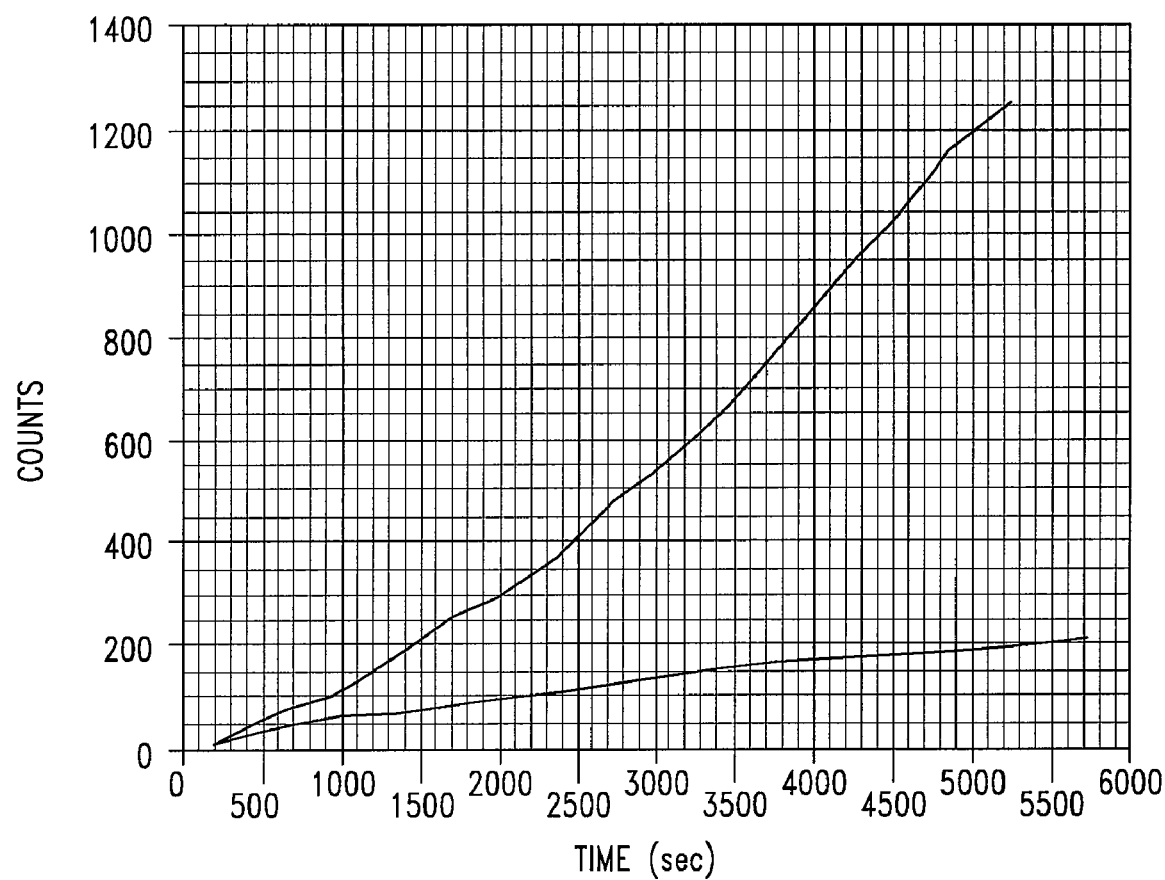
FIG. 8 is a plot demonstrating the effectiveness of paired bellows pump mixing methodology as evidenced by capture of CD45 cells from spiked biological fluids with magnetic beads. The method and results are discussed in Example 2.

Turning to FIG. 8, data is presented demonstrating the use of the dual bellows pump mixers as a tool for concentration of a cellular analyte. Method details are presented in Example 2. The data show that CD45 ligand-expressing cells are effectively captured by mixing cells with affinity capture beads in a device of the invention.

Figure 9:
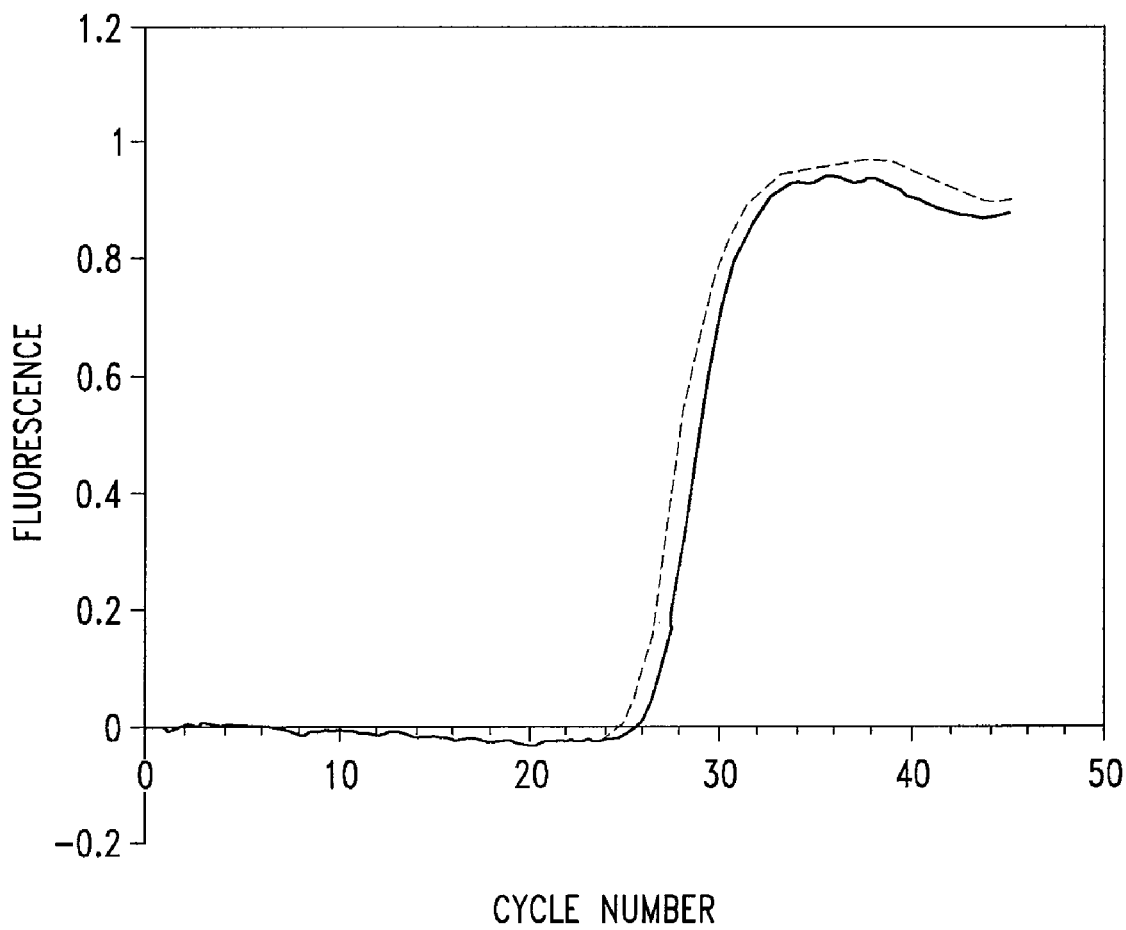
FIG. 9 is a plot demonstrating capture of *E. coli* cells from a fecal test sample with magnetic beads. The method and results are discussed in Example 3.

In FIG. 9, data is presented demonstrating that the *E. coli* serotype causative for enterohemorrhagic diarrhea is readily captured for detection from stool by mixing stool with affinity capture beads in a device of the present invention. Method details are presented in Example 3.

Figure 10:
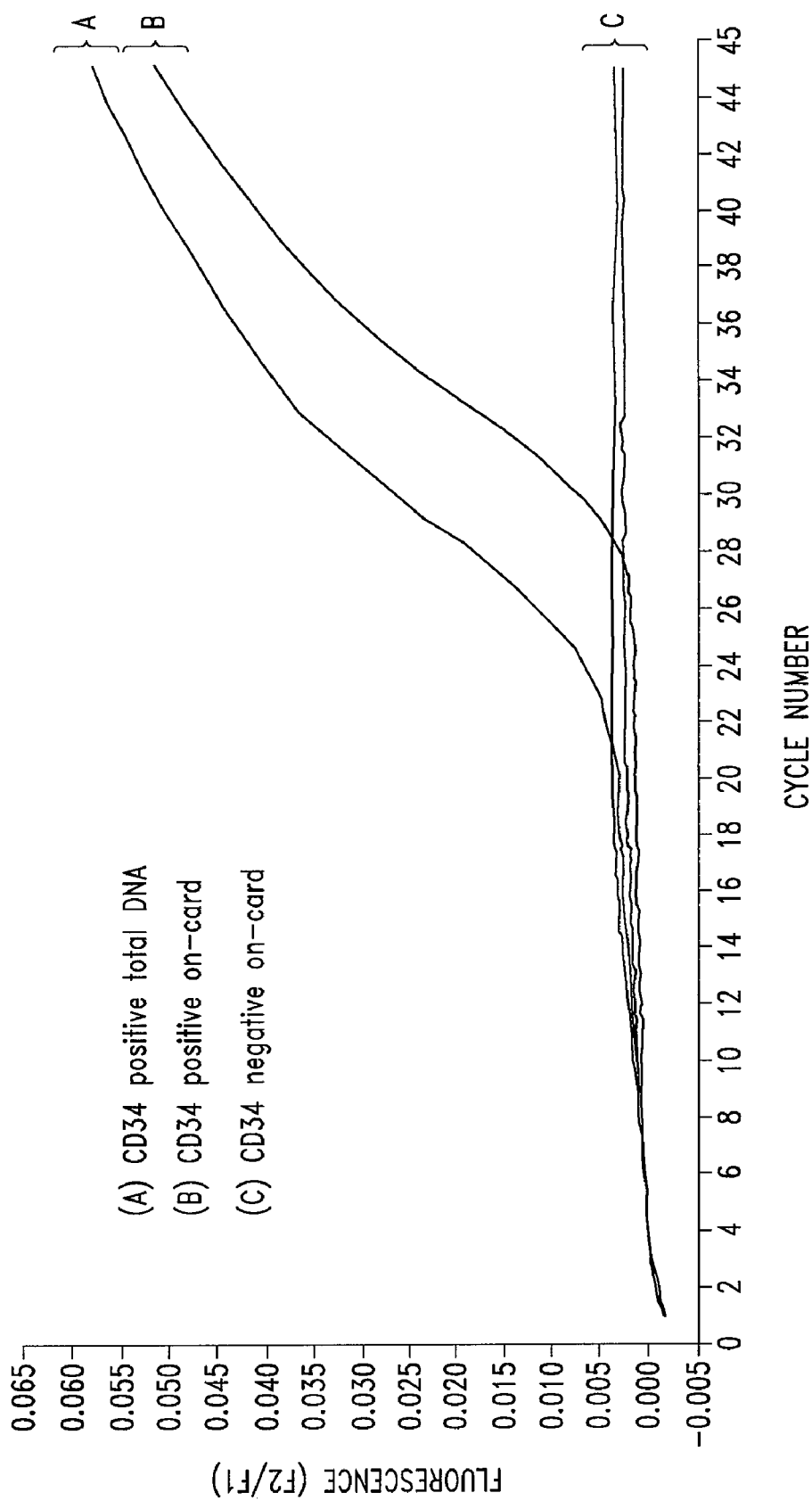
FIG. 10 is a plot demonstrating capture of CD34 cells from a blood sample with magnetic beads. The method and results are discussed in Example 4.

In FIG. 10, data is presented demonstrating that CD34 ligand-expressing cells characteristic of certain cancers are readily captured by mixing cells with affinity capture beads in a device of the present invention. Method details are presented in Example 4.

EXAMPLES

Example 1

Transition to Turbulent Flow

A classical way to detect the pipe-flow transition for a fluid is to inject a stream of dye into the moving fluid and to observe the wavering of the dye stream as it flows down the pipe. In the present experiment with particles, direct visualization of particle motion is also a very straightforward way of observing laminar flow and turbulence. Motion in the laminar regime is characterized by parallel particle trajectories, and motion in a turbulent transitional "puff" represents strong mixing in the radial direction. Similar observations can also be made as laminar flow breaks up as fluid exits from a pipe into a bulk fluid receiving vessel.

Flows in microfluidic structures are laminar and allow mixing by diffusion along boundary layers and interfaces (a phenomenon described in detail in U.S. Pat. No. 5,972,710 to Wiegl and co-assigned). However, such phenomena present a problem in microfluidic devices where bulk mixing or comminution of a sample and reagents or beads is required.

The Reynolds number (Re) compares the relative importance of inertial and viscous forces; in low-Reynolds-number flows, viscous drag dominates over inertial phenomena. Reynolds number, in fact, can decrease in the presence of significant populations of beads. Bead populations in some of the experiments reported here were in the order of $10^7$ to $10^9$ beads/mL.

Low-Reynolds-number flows essentially preclude turbulence as a mixing phenomenon. Here we report a hybrid device that functions effectively in fluid:particle mixing with intermittent pulsed flow at Reynolds numbers of 1000 or less; for samples containing cells—more preferentially 200 or less. Reynolds number is a dimensionless coefficient. Suitable mixing conditions correspond to intermittent pulsed flow with shear rates (as velocity divided by diameter) of less than 3000 $s^{-1}$; for samples containing cells—more preferentially less than 200 $s^{-1}$. Wall shear stress may also be considered.

An exemplary device similar to that of FIG. 3 was constructed. The device consisted of a pair of bellows pumps, separated by a flow-restricting aperture, and connected to inlet and outlet ports by microfluidic channels and valves. A bead suspension and sample fluid was introduced. All valves were then closed, and pneumatically actuated diaphragms were used to force fluid back and forth between the bellows pump chambers. In the initial design selected for developmental work, the aperture had the following dimensions:

TABLE I

Aperture Dimensions

| Aperture Dimension | (inch) | (mm) |
|---|---|---|
| Width (X) | 0.080 | 2.032 |
| Depth (Z) | 0.072 | 1.829 |
| Length (L) | 0.114 | 2.896 |

Here, L is about 3 mm and the channel is about 2×2 mm, dimensions chosen to prevent blockage by solid debris characteristic of fecal suspensions. Nominal pulse peak fluid velocity in a channel of the specified cross-sectional dimensions is calculated to be 100 cm/sec when a 10 psi pressure pulse is applied. This corresponds to Re=200, well within expected laminar flow conditions. Shear rate is about 100 $s^{-1}$.

Under these conditions, beads and particles moving through the orifice experience laminar, focused flow, and denser beads moving with the core fluid can develop significant kinetic energy, a force exceeding the fluid kinetic energy as an inertial component upon exit from the aperture.

Ribbon flow was readily observed. Magnetic bead populations were observed forming focused dark streams passaging through the aperture, exiting the aperture as a fluid jet, and dispersing as vortices in the bulk fluid of the receiving chamber. In non-Newtonian fluids, the coherence of this jet and surrounding vortices was even more apparent, due to the increases in viscosity attendant upon the presence of beads and polymer. These vortices or "turbulent puffs" are characteristic of transition to turbulent flow, and there was no doubt that the bead suspension was an aid in mixing of soluble and suspended components such as molecules and cells. Turbulent mixing increases the surface area over which beads and analytes can interact. As judged by eye, suspensions were homogenized within 3 to 4 cycles through the mixer.

While several parameters such as aperture dimensions, actuation pressure, pulse shape, bellows chamber diameter (as "effective diameter"), can be varied to adjust mixing and shear forces for particular samples and applications, an illustration showing the use of pulse frequency and total duration is shown in the following table. Pulse duration refers to the time component of a half wave. The length of the mixing period (sec/assay) is calculated by dividing the total cycles per assay by the pulse frequency.

TABLE II

Programmed Pneumatic Pulse Regimes

| | Frequency (Hz) | Actuation Pressure | Total cycles per assay | Pulse Duration | Assay Time (sec/assay) |
|---|---|---|---|---|---|
| Blood | 0.2 Hz | 10 psi/10 in Hg | 12 | 2.5 sec | 60 sec |
| Liquified Feces | 1 Hz | 10 psi/10 in Hg | 60 | 0.5 sec | 60 sec |

While larger actuation pressures were optimal for comminution of stool and dispersion of bacterial load, similar pulse pressures were found to be suboptimal for interaction of cells in blood with affinity capture beads. Excessive shear stress at the interfacial layer can result in disruption of cells or the cell/bead capture complexes. Improved conditions can be obtained, for example, by reducing the pneumatic actuation pressure across the aperture, the shear rate, or the temperature. From actuation pressure, linear flow rate, and aperture dimensions, operating parameters such as shear and flow rate can be calculated for the desired mixing conditions. Optimization of conditions in which bead populations are present may benefit from an experimental approach (see for example: Lu H et al. 2004. Microfluidic shear devices for quantitative analysis of cell adhesion. Anal Chem 76:5257-64; Staben M E et al. 2005. Particle transport in Poiseuille flow in narrow channels. Intl J Multiphase Flow 31:529-47; Matas J P et al. 2003. Transition to turbulence in particulate pipe flow. Phys. Rev. Lett. 90:14501-505; and references cited therein), as described above for blood and stool.

Interestingly, for blood (viscosity=0.036 dyne-s/cm$^2$), shear rates of 500 s$^{-1}$ are sufficient to lyse erythrocytes, but are not hemolytic when alternated with periods of shear rates less than 300 s$^{-1}$ (Kameneva M et al. 2004. Effects of turbulent stresses upon mechanical hemolysis: experimental and computational analysis. ASAIO J 50:418-423; Hashimoto S. 1989. Erythrocyte destruction under periodically fluctuating shear rate: comparative study with constant shear rate. Artif Organs 13:458-63). Also, prolonged wall shear stress of 100-600 dynes/cm$^2$ at Reynolds numbers of 100 to 300 has a significant impact on leukocyte integrity and viability, but pulsed exposure does not (Carter J et al. 2003. Short exposure time sensitivity of white cells to shear stress. ASAIO J 49:687-91; Dewitz T S et al. 1977. Mechanical trauma in leukocytes. J Lab Clin Med 90:728-36). Leukocytes are regarded as a more general indicator of cell sensitivity than erythrocytes. Thus the intermittent pulse condition inherent in the mixers described here is expected to improve viability and integrity of recovered cells.

With regard to fecal material, Reynolds numbers in excess of 200 and more preferentially of 500 may be desirable. An aperture size of 2×2 mm with a nominal pulse peak flow Reynolds number of 100 was selected for this example and was used in the device of Example 3. The devices and apparatuses described here may also be configured for other applications.

Example 2

CD45 Depletion Using a Dual Bellows Mixing Device

Experimental Cartridge Protocol:

White cells were isolated from blood 5 mL with a 5 min room temperature lysis using Gentra RBC lysis solution. After two washes with phosphate buffered saline (PBS) the white blood cell (WBC) pellet was resuspended in 1 ml of PBS. About 10,000 SW480 cells (Cd45+) in 100 uL buffer were added to 100 ul of the resuspended WBC pellet and the mixture was transferred to a dual bellows mixing cartridge of the present invention. All reagents and apparatus were chilled to 4° C. for the experiment. CD45 affinity capture magnetic beads 100 uL (Dynal MyOne®, Cat No. 111.53, 4×10$^8$ beads/mL) were then added. Bead population in the mixer was thus about 4×10$^7$ beads in a volume of 200 uL, with a cell:bead ratio of about 1:4000. The sample:bead suspension was mixed for four minutes using an automated apparatus compatible with the cartridge. A magnet was applied to the cartridge to trap the beads and the depleted fluid matrix was collected for analysis. As a control, a second cartridge was run without affinity capture beads. To label the cells for fluorescence sorting, CD45-PE label (BD Biosciences 555820) was added to each supernatant generated in the above protocol. A fluorescence cell sorter (US patent application number 20060246575 and 20030175980) was then used to assess relative counts.

Results presented in FIG. 8 show (top curve, without beads) WBC population with SW480 spike, (middle curve, with beads) depletion following treatment with CD45 affinity capture beads, and (bottom curve) WBC population without spike.

Manufacturers Protocol:

In a second experiment, the above method was compared with a screw-cap tube mixing protocol supplied by the manufacturer of the beads and run in parallel. We combined 100 ul of SW480 spiked WBC pellet and 100 ul of CD45 ligand capture magnetic beads and rotated the tube end-over-end at 4° C. for 30 min. A magnet was applied to trap the beads with captured CD45 cells and the supernatant was saved for analysis. 20 ul of CD45-PE label (BD Biosciences 555820) was added to the supernatant (about 100 ul), and the stained cell population was counted as before. Depletion by both methods was similar but the result was obtained with a 4 minute incubation with the dual bellows cartridge mixer versus a 30 min incubation with the rotating mixer recommended by the manufacturer of the affinity capture beads.

Example 3

Capture of *E. coli* with O157:H7 Serotype-Specific Antibody

Affinity Capture Bead Preparation:

Dynal MyOne® Tosylactivated beads were obtained from the manufacturer (Dynal ASA, Oslo Norway) and derivatized with Anti-O157:H7 antibody (US Biologicals, Swampscott Mass.) by the suggested protocol. Per 1 mg of beads, 40 mg of antibody was used. Bead diameter is 1.08 um.

Dual Bellows Pump Mixing and Capture Device Description:

The mixing and capture cartridge tested had three parallel dual bellows pump mixing devices and supporting fluidic circuitry, so that three experiments could be run side-by-side in the apparatus. Each mixing device was provided with a pipet port, a pair of bellows pumps with interconnecting aperture, a fill port for magnetic beads, and pneumatic pulse actuation ports for the mixing chamber and valves. The device was placed into a microFlow™ manifold (Micronics, Inc. Redmond Wash.) apparatus so that the microfluidic valves and actuation lines could be controlled via computer using an automated workstation. Microfluidic valves and the actuation line were driven by 10 psi pressure and 10 in Hg vacuum.

Cartridge Operation:

Beads and sample were added manually to the mixing chamber. The workstation closed the microfluidic valves to seal the system and the supplied alternating vacuum and pressure to the actuation line at approximately 1 full cycle per second, forcing the sample (diluted stool spiked with pathogenic *E. coli* and bead suspension) back and forth through the flow aperture. Nominal maximal volume of the mixing chamber was about 600 µl and sample volume was about 400 uL. After 60 seconds of mixing, a magnetic field was applied to the top of the card (here a rare earth NdFeB magent was used) to trap the magnetic beads and any bound cells during rinsing. Microfluidic valves were opened so that the waste fluid matrix could be discarded. A wash solution of 400 µl PBS with 0.05% Tween20 was added through the pipet fill hole and the magnetic field was removed. The bead suspension in wash buffer was pushed back and forth for 60 seconds through the flow aperture to re-suspend the beads. The magnetic field was applied again to the top of the card to separate the magnetic beads and any bound cells from the discarded wash solution. The wash process was repeated 3 times. After magnetic separation and removal of the final wash solution, a lysis solution was added and mixed with the beads in the cartridge to release any nucleic acid material from the bacteria bound to the beads. The magnet was used to trap the beads while the lysis solution containing cell lysate was recovered via pipet for DNA purification and rttPCR analysis.

Manufacturer's Procedure:

The Dynal protocol calls for vortexing samples and beads in a test tube for up to 30 min and then separating and washing the beads while using a magnet to hold the beads in place. Following washing, cells captured by the beads were lysed and quantitated by rtPCR after DNA purification.

Results:

Data is presented in FIG. 9. Bacterial cell capture in the experimental mixing device (solid line) was just as efficient as the manufacturer's method (dotted line), but incubation time was reduced from 30 min to 60 sec. In work done with O157:H7 positive stool samples, average Lightcycler crossing values were 28.8 and 29.0 cycles for on-card processed samples and off-card processed samples, respectively. Serial diluted quantitative standards of 10-fold increments give differences of approximately 3.3 cycles. Therefore, the observed difference of 0.2 cycles between on-card and off-card crossing values are negligible.

Example 4

Capture of CD34 Cells from Blood

Affinity Capture Bead Preparation:

Dynal MyOne® Beads (Cat No 113.01, $4 \times 10^8$ beads/mL) specific for capture of CD34 expressing leukocytes were prepared according to the manufacturer's recommendations. CD34 antigen is specific for hematogenic progenitor cells, and certain thymocytes and endothelial cell populations.

Cell Culture:

A CD34-positive cell line having G6PD marker (by PCR) was grown in culture. These cells were either added directly to lysis buffer (total DNA, maximum possible yield), or mixed with blood and enriched by magnetic bead capture either 1) in a dual bellows pump capture and mixing cartridge; or 2) by the manufacture's recommended procedure in a test tube. Lightcycler® assay was used for evaluation of bead capture following isolation of G6PD transcripts with RNeasy (Qiagen, Venlo, The Netherlands) and cDNA synthesis by established protocols. As shown in FIG. 10, on-card (i.e., with dual bellows mixing cartridge) mixing did not capture as much of the marker as the manufacturer's recommended procedure, but was clearly positive in the assay.

Although the above description and drawings contain specificities, these specificities should not be construed as limitations on the scope of the invention, but rather as exemplifications of embodiments of the invention. That is to say, the foregoing description of the invention is exemplary for purposes of illustration and explanation. Without departing from the spirit and scope of this invention, one skilled in the art can make changes and modifications to the invention to adapt it to various usages and conditions without inventive step. Any such changes and modifications are properly, equitably, and intended to be, within the full range of equivalence of the following claims. Thus the scope of the invention should be determined by the appended claims and their legal equivalents, when taken in light of the above specification.

We claim:

1. A microfluidic cartridge comprising:
   a) a first bellows pump with a pump cavity bisected in coronal plane by a first elastomeric diaphragm, said first diaphragm dividing said pump cavity of said first bellows pump into a first half-chamber and a second half-chamber;
   b) a second bellows pump with a pump cavity bisected in coronal plane by a second elastomeric diaphragm, said second diaphragm dividing said pump cavity of said second bellows pump into a first half-chamber and a second half-chamber;
   c) a flow-restricting aperture fluidly interconnecting said first half-chamber of said first bellows pump with said first half-chamber of said second bellows pump, said flow-restricting aperture having a depth, width and length such that fluid flow within the flow-restricting aperture is laminar;
   d) an inlet fluidly connected to said first half chamber of said first bellows pump, wherein said inlet is comprised of a microfluidic channel with valve;
   e) a pneumatic member pneumatically connected to said second half chamber of said first bellows pump, wherein said pneumatic element is selected from the group consisting of a microchannel and a vent; and
   f) a pneumatic member pneumatically connected to said second half chamber of said second bellows pump, wherein said pneumatic element is selected from the group consisting of a microchannel and a vent, wherein said cartridge is configured to receive pneumatic pulses from a pneumatic pulse generator programmed to actuate the first diaphragm with pneumatic pulses such that fluid flow within the flow-restricting aperture is laminar, but transitions to turbulent flow upon exiting said flow-restricting aperture and into said first half-chambers of said first and second bellows pumps.

2. A microfluidic cartridge of claim 1, further comprising dehydrated beads.

3. A microfluidic cartridge of claim 2, wherein said dehydrated beads are affinity capture beads.

4. A microfluidic cartridge of claim 3, wherein said affinity capture beads are paramagnetic beads.

5. A microfluidic cartridge of claim 3, wherein said affinity capture beads have affinity for target analyte.

6. A microfluidic cartridge of claim 5, wherein said target analyte is selected from the group consisting of eukaryotic cell, bacterial cell, virus, macromolecule, antigen, antibody, epitope, nucleic acid, metabolite, small molecule, and drug.

7. A microfluidic cartridge of claim 3, wherein said affinity capture beads have affinity for a ligand.

8. A microfluidic cartridge of claim 7, wherein said ligand further comprises a member selected from the group consisting of eukaryotic cell, bacterial cell, virus, macromolecule, antigen, antibody, epitope, nucleic acid, metabolite, small molecule, and drug.

9. A microfluidic cartridge of claim 7, wherein said ligand further comprises a target analyte selected from the group consisting of eukaryotic cell, bacterial cell, virus, macromolecule, antigen, antibody, epitope, nucleic acid, metabolite, small molecule, and drug.

10. A microfluidic cartridge of claim 3, wherein said affinity capture beads have affinity for a nucleic acid.

11. A microfluidic cartridge of claim 3, wherein said affinity capture beads have affinity for an antigen.

12. A microfluidic cartridge of claim 1, wherein said pneumatic member connected to said second half-chamber of said first bellows pump is a microchannel and said pneumatic member connected to said second half-chamber of said second bellows pump is a vent.

13. A microfluidic cartridge of claim 1, further comprising molded members.

14. A microfluidic cartridge of claim 13, wherein said molded members comprise the walls of said aperture and bellows pump cavities.

15. A kit comprising a microfluidic cartridge of claim 1, and further comprising a means for detecting a target analyte.

* * * * *

UNITED STATES PATENT AND TRADEMARK OFFICE
CERTIFICATE OF CORRECTION

| | |
|---|---|
| PATENT NO. | : 7,763,453 B2 |
| APPLICATION NO. | : 11/562611 |
| DATED | : July 27, 2010 |
| INVENTOR(S) | : John Clemmens et al. |

It is certified that error appears in the above-identified patent and that said Letters Patent is hereby corrected as shown below:

Column 24, Line 22
"d) an inlet fluidly connected to said first half chamber of" should read, --d) an inlet fluidly connected to said first half-chamber of--.

Column 24, Line 26
"second half chamber of said first bellows pump, wherein" should read, --second half-chamber of said first bellows pump, wherein--.

Column 24, Line 30
"second half chamber of said second bellows pump," should read, --second half-chamber of said second bellows pump,--.

Signed and Sealed this
Eighth Day of March, 2011

David J. Kappos
*Director of the United States Patent and Trademark Office*